US012807671B2

(12) United States Patent
Yang et al.

(10) Patent No.: US 12,807,671 B2
(45) Date of Patent: Nov. 24, 2026

(54) HUMANIZED ACE2-Fc FUSION PROTEIN FOR TREATMENT AND PREVENTION OF SARS-CoV-2 INFECTION

(71) Applicants: ACADEMIA SINICA, Taipei City (TW); NATIONAL TAIWAN UNIVERSITY, Taipei City (TW)

(72) Inventors: Pan-Chyr Yang, Taipei City (TW); Sui-Yuan Chang, Taipei City (TW); Kuo-Yen Huang, Taipei City (TW)

(73) Assignees: ACADEMIA SINICA, Taipei City (TW); NATIONAL TAIWAN UNIVERSITY, Taipei City (TW)

( * ) Notice: Subject to any disclaimer, the term of this patent is extended or adjusted under 35 U.S.C. 154(b) by 442 days.

(21) Appl. No.: 18/001,947

(22) PCT Filed: Jun. 15, 2021

(86) PCT No.: PCT/US2021/037344

§ 371 (c)(1),
(2) Date: Dec. 15, 2022

(87) PCT Pub. No.: WO2021/257512

PCT Pub. Date: Dec. 23, 2021

(65) Prior Publication Data

US 2023/0235007 A1 Jul. 27, 2023

Related U.S. Application Data

(60) Provisional application No. 63/039,228, filed on Jun. 15, 2020.

(51) Int. Cl.

| | |
|---|---|
| ***C07K 14/705*** | (2006.01) |
| ***A61K 38/17*** | (2006.01) |
| ***A61K 38/20*** | (2006.01) |
| ***A61K 45/06*** | (2006.01) |
| ***A61K 47/64*** | (2017.01) |
| ***A61P 31/14*** | (2006.01) |
| ***C07K 14/55*** | (2006.01) |

(52) U.S. Cl.

CPC .......... *C07K 14/705* (2013.01); *A61K 38/177* (2013.01); *A61K 38/2013* (2013.01); *A61K 45/06* (2013.01); *A61K 47/642* (2017.08); *A61K 47/6425* (2017.08); *A61P 31/14* (2018.01); *C07K 14/55* (2013.01); *C07K 2319/02* (2013.01); *C07K 2319/30* (2013.01)

(58) Field of Classification Search

None

See application file for complete search history.

(56) References Cited

U.S. PATENT DOCUMENTS

| | | | | |
|---|---|---|---|---|
| 10,428,131 | B2 * | 10/2019 | Stewart .................. | A61P 37/04 |
| 10,676,511 | B2 | 6/2020 | Gershoni et al. | |
| 12,123,036 | B2 * | 10/2024 | Batlle ................ | A61K 38/4813 |

FOREIGN PATENT DOCUMENTS

| | | |
|---|---|---|
| KR | 10-2017-0085588 A | 7/2017 |
| WO | WO 2016/086021 A1 | 6/2016 |
| WO | WO 2016/138160 A1 | 9/2016 |

OTHER PUBLICATIONS

[No Author Listed] BAS37890. Database Geneseq. Human ACE2 truncated mature protein, SEQ ID: 27. XP002811636, retrieved from EBI accession No. GSP: BAS37890, Oct. 10, 2013, 1 page.

Extended European Search Report for European Patent App. No. 21826814.2, dated Jun. 14, 2024 (8 pages).

Liu, P., et al., Novel ACE2-Fc chimeric fusion provides long-lasting hypertension control and organ protection in mouse models of systemic renin angiotensin system activation. Kidney Int. Jul. 2018;94(1):114-125. doi: 10.1016/j.kint.2018.01.029. Epub Apr. 22, 2018.

Procko, E., The sequence of human ACE2 is suboptimal for binding the S spike protein of SARS coronavirus 2. Version 3. bioRxiv. Preprint. May 11, 2020, XP055892919, 21 pages.

[No Author Listed], NCBI GenBank Accession No. BAB40370.1 "ACE2 [*Homo sapiens*]". Apr. 14, 2021. 2 pages. Accessible at ncbi.nlm.nih.gov/protein/bab40370.1.

Huang et al., Humanized COVID-19 decoy antibody effectively blocks viral entry and prevents SARS-CoV-2 infection. EMBO Mol Med. Jan. 11, 2021;13(1):e12828. Epub Nov. 30, 2020.

Lei et al., Neutralization of SARS-CoV-2 spike pseudotyped virus by recombinant ACE2-Ig. Nat Commun. Apr. 24, 2020;11(1):2070(1-5).

* cited by examiner

*Primary Examiner* — Michail A Belyavskyi

(74) *Attorney, Agent, or Firm* — McDermott Will & Schulte LLP; Charles D. Larsen; Yuhe Liu

(57) ABSTRACT

Disclosed herein are ACE2-Fc fusion polypeptides that contain at least one binding site for a spike protein of a coronavirus and methods of using such for therapeutic and/or diagnostic purposes. Also provided herein are methods for producing such fusion polypeptides.

15 Claims, 23 Drawing Sheets

Specification includes a Sequence Listing.

SEQUENCE LISTING

```
<160> NUMBER OF SEQ ID NOS: 6

<210> SEQ ID NO 1
<211> LENGTH: 805
<212> TYPE: PRT
<213> ORGANISM: Homo sapiens
```

<400> SEQUENCE: 1

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400
```

```
His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
        675                 680                 685

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
            740                 745                 750

Ile Val Val Gly Ile Val Ile Leu Ile Phe Thr Gly Ile Arg Asp Arg
        755                 760                 765

Lys Lys Lys Asn Lys Ala Arg Ser Gly Glu Asn Pro Tyr Ala Ser Ile
    770                 775                 780

Asp Ile Ser Lys Gly Glu Asn Asn Pro Gly Phe Gln Asn Thr Asp Asp
785                 790                 795                 800

Val Gln Thr Ser Phe
                805
```

<210> SEQ ID NO 2
<211> LENGTH: 598
<212> TYPE: PRT
<213> ORGANISM: Homo sapiens

<400> SEQUENCE: 2

Gln Ser Thr Ile Glu Glu Gln Ala Lys Thr Phe Leu Asp Lys Phe Asn
1               5                   10                  15

His Glu Ala Glu Asp Leu Phe Tyr Gln Ser Ser Leu Ala Ser Trp Asn
            20                  25                  30

Tyr Asn Thr Asn Ile Thr Glu Glu Asn Val Gln Asn Met Asn Asn Ala
        35                  40                  45

Gly Asp Lys Trp Ser Ala Phe Leu Lys Glu Gln Ser Thr Leu Ala Gln
    50                  55                  60

Met Tyr Pro Leu Gln Glu Ile Gln Asn Leu Thr Val Lys Leu Gln Leu
65                  70                  75                  80

Gln Ala Leu Gln Gln Asn Gly Ser Ser Val Leu Ser Glu Asp Lys Ser
                85                  90                  95

Lys Arg Leu Asn Thr Ile Leu Asn Thr Met Ser Thr Ile Tyr Ser Thr
            100                 105                 110

Gly Lys Val Cys Asn Pro Asp Asn Pro Gln Glu Cys Leu Leu Leu Glu
        115                 120                 125

Pro Gly Leu Asn Glu Ile Met Ala Asn Ser Leu Asp Tyr Asn Glu Arg
    130                 135                 140

Leu Trp Ala Trp Glu Ser Trp Arg Ser Glu Val Gly Lys Gln Leu Arg
145                 150                 155                 160

Pro Leu Tyr Glu Glu Tyr Val Val Leu Lys Asn Glu Met Ala Arg Ala
                165                 170                 175

Asn His Tyr Glu Asp Tyr Gly Asp Tyr Trp Arg Gly Asp Tyr Glu Val
            180                 185                 190

Asn Gly Val Asp Gly Tyr Asp Tyr Ser Arg Gly Gln Leu Ile Glu Asp
        195                 200                 205

Val Glu His Thr Phe Glu Glu Ile Lys Pro Leu Tyr Glu His Leu His
    210                 215                 220

Ala Tyr Val Arg Ala Lys Leu Met Asn Ala Tyr Pro Ser Tyr Ile Ser
225                 230                 235                 240

Pro Ile Gly Cys Leu Pro Ala His Leu Leu Gly Asp Met Trp Gly Arg
                245                 250                 255

Phe Trp Thr Asn Leu Tyr Ser Leu Thr Val Pro Phe Gly Gln Lys Pro
            260                 265                 270

Asn Ile Asp Val Thr Asp Ala Met Val Asp Gln Ala Trp Asp Ala Gln
        275                 280                 285

Arg Ile Phe Lys Glu Ala Glu Lys Phe Phe Val Ser Val Gly Leu Pro
    290                 295                 300

Asn Met Thr Gln Gly Phe Trp Glu Asn Ser Met Leu Thr Asp Pro Gly
305                 310                 315                 320

Asn Val Gln Lys Ala Val Cys His Pro Thr Ala Trp Asp Leu Gly Lys
                325                 330                 335

Gly Asp Phe Arg Ile Leu Met Cys Thr Lys Val Thr Met Asp Asp Phe
            340                 345                 350

Leu Thr Ala His His Glu Met Gly His Ile Gln Tyr Asp Met Ala Tyr
        355                 360                 365

Ala Ala Gln Pro Phe Leu Leu Arg Asn Gly Ala Asn Glu Gly Phe His
    370                 375                 380

Glu Ala Val Gly Glu Ile Met Ser Leu Ser Ala Ala Thr Pro Lys His
385 390 395 400

Leu Lys Ser Ile Gly Leu Leu Ser Pro Asp Phe Gln Glu Asp Asn Glu
405 410 415

Thr Glu Ile Asn Phe Leu Leu Lys Gln Ala Leu Thr Ile Val Gly Thr
420 425 430

Leu Pro Phe Thr Tyr Met Leu Glu Lys Trp Arg Trp Met Val Phe Lys
435 440 445

Gly Glu Ile Pro Lys Asp Gln Trp Met Lys Lys Trp Trp Glu Met Lys
450 455 460

Arg Glu Ile Val Gly Val Val Glu Pro Val Pro His Asp Glu Thr Tyr
465 470 475 480

Cys Asp Pro Ala Ser Leu Phe His Val Ser Asn Asp Tyr Ser Phe Ile
485 490 495

Arg Tyr Tyr Thr Arg Thr Leu Tyr Gln Phe Gln Phe Gln Glu Ala Leu
500 505 510

Cys Gln Ala Ala Lys His Glu Gly Pro Leu His Lys Cys Asp Ile Ser
515 520 525

Asn Ser Thr Glu Ala Gly Gln Lys Leu Phe Asn Met Leu Arg Leu Gly
530 535 540

Lys Ser Glu Pro Trp Thr Leu Ala Leu Glu Asn Val Val Gly Ala Lys
545 550 555 560

Asn Met Asn Val Arg Pro Leu Leu Asn Tyr Phe Glu Pro Leu Phe Thr
565 570 575

Trp Leu Lys Asp Gln Asn Lys Asn Ser Phe Val Gly Trp Ser Thr Asp
580 585 590

Trp Ser Pro Tyr Ala Asp
595

<210> SEQ ID NO 3
<211> LENGTH: 227
<212> TYPE: PRT
<213> ORGANISM: Homo sapiens

<400> SEQUENCE: 3

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Ser Arg Glu Glu Met Thr Lys Asn Gln Val Ser
130 135 140

Leu Thr Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 4
<211> LENGTH: 831
<212> TYPE: PRT
<213> ORGANISM: Artificial Sequence
<220> FEATURE:
<223> OTHER INFORMATION: Synthetic

<400> SEQUENCE: 4

Ala Ser Gln Ser Thr Ile Glu Glu Gln Ala Lys Thr Phe Leu Asp Lys
1 5 10 15

Phe Asn His Glu Ala Glu Asp Leu Phe Tyr Gln Ser Ser Leu Ala Ser
20 25 30

Trp Asn Tyr Asn Thr Asn Ile Thr Glu Glu Asn Val Gln Asn Met Asn
35 40 45

Asn Ala Gly Asp Lys Trp Ser Ala Phe Leu Lys Glu Gln Ser Thr Leu
50 55 60

Ala Gln Met Tyr Pro Leu Gln Glu Ile Gln Asn Leu Thr Val Lys Leu
65 70 75 80

Gln Leu Gln Ala Leu Gln Gln Asn Gly Ser Ser Val Leu Ser Glu Asp
85 90 95

Lys Ser Lys Arg Leu Asn Thr Ile Leu Asn Thr Met Ser Thr Ile Tyr
100 105 110

Ser Thr Gly Lys Val Cys Asn Pro Asp Asn Pro Gln Glu Cys Leu Leu
115 120 125

Leu Glu Pro Gly Leu Asn Glu Ile Met Ala Asn Ser Leu Asp Tyr Asn
130 135 140

Glu Arg Leu Trp Ala Trp Glu Ser Trp Arg Ser Glu Val Gly Lys Gln
145 150 155 160

Leu Arg Pro Leu Tyr Glu Glu Tyr Val Val Leu Lys Asn Glu Met Ala
165 170 175

Arg Ala Asn His Tyr Glu Asp Tyr Gly Asp Tyr Trp Arg Gly Asp Tyr
180 185 190

Glu Val Asn Gly Val Asp Gly Tyr Asp Tyr Ser Arg Gly Gln Leu Ile
195 200 205

Glu Asp Val Glu His Thr Phe Glu Glu Ile Lys Pro Leu Tyr Glu His
210 215 220

Leu His Ala Tyr Val Arg Ala Lys Leu Met Asn Ala Tyr Pro Ser Tyr
225 230 235 240

Ile Ser Pro Ile Gly Cys Leu Pro Ala His Leu Leu Gly Asp Met Trp
245 250 255

Gly Arg Phe Trp Thr Asn Leu Tyr Ser Leu Thr Val Pro Phe Gly Gln
260 265 270

```
Lys Pro Asn Ile Asp Val Thr Asp Ala Met Val Asp Gln Ala Trp Asp
        275                 280                 285

Ala Gln Arg Ile Phe Lys Glu Ala Glu Lys Phe Phe Val Ser Val Gly
    290                 295                 300

Leu Pro Asn Met Thr Gln Gly Phe Trp Glu Asn Ser Met Leu Thr Asp
305                 310                 315                 320

Pro Gly Asn Val Gln Lys Ala Val Cys His Pro Thr Ala Trp Asp Leu
                325                 330                 335

Gly Lys Gly Asp Phe Arg Ile Leu Met Cys Thr Lys Val Thr Met Asp
            340                 345                 350

Asp Phe Leu Thr Ala His His Glu Met Gly His Ile Gln Tyr Asp Met
        355                 360                 365

Ala Tyr Ala Ala Gln Pro Phe Leu Leu Arg Asn Gly Ala Asn Glu Gly
    370                 375                 380

Phe His Glu Ala Val Gly Glu Ile Met Ser Leu Ser Ala Ala Thr Pro
385                 390                 395                 400

Lys His Leu Lys Ser Ile Gly Leu Leu Ser Pro Asp Phe Gln Glu Asp
                405                 410                 415

Asn Glu Thr Glu Ile Asn Phe Leu Leu Lys Gln Ala Leu Thr Ile Val
            420                 425                 430

Gly Thr Leu Pro Phe Thr Tyr Met Leu Glu Lys Trp Arg Trp Met Val
        435                 440                 445

Phe Lys Gly Glu Ile Pro Lys Asp Gln Trp Met Lys Lys Trp Trp Glu
    450                 455                 460

Met Lys Arg Glu Ile Val Gly Val Val Glu Pro Val Pro His Asp Glu
465                 470                 475                 480

Thr Tyr Cys Asp Pro Ala Ser Leu Phe His Val Ser Asn Asp Tyr Ser
                485                 490                 495

Phe Ile Arg Tyr Tyr Thr Arg Thr Leu Tyr Gln Phe Gln Phe Gln Glu
            500                 505                 510

Ala Leu Cys Gln Ala Ala Lys His Glu Gly Pro Leu His Lys Cys Asp
        515                 520                 525

Ile Ser Asn Ser Thr Glu Ala Gly Gln Lys Leu Phe Asn Met Leu Arg
    530                 535                 540

Leu Gly Lys Ser Glu Pro Trp Thr Leu Ala Leu Glu Asn Val Val Gly
545                 550                 555                 560

Ala Lys Asn Met Asn Val Arg Pro Leu Leu Asn Tyr Phe Glu Pro Leu
                565                 570                 575

Phe Thr Trp Leu Lys Asp Gln Asn Lys Asn Ser Phe Val Gly Trp Ser
            580                 585                 590

Thr Asp Trp Ser Pro Tyr Ala Asp Val Glu Val Asp Asp Lys Thr His
        595                 600                 605

Thr Cys Pro Pro Cys Pro Ala Pro Glu Leu Leu Gly Gly Pro Ser Val
    610                 615                 620

Phe Leu Phe Pro Pro Lys Pro Lys Asp Thr Leu Met Ile Ser Arg Thr
625                 630                 635                 640

Pro Glu Val Thr Cys Val Val Val Asp Val Ser His Glu Asp Pro Glu
                645                 650                 655

Val Lys Phe Asn Trp Tyr Val Asp Gly Val Glu Val His Asn Ala Lys
            660                 665                 670

Thr Lys Pro Arg Glu Glu Gln Tyr Asn Ser Thr Tyr Arg Val Val Ser
        675                 680                 685
```

-continued

```
Val Leu Thr Val Leu His Gln Asp Trp Leu Asn Gly Lys Glu Tyr Lys
    690                 695                 700

Cys Lys Val Ser Asn Lys Ala Leu Pro Ala Pro Ile Glu Lys Thr Ile
705                 710                 715                 720

Ser Lys Ala Lys Gly Gln Pro Arg Glu Pro Gln Val Tyr Thr Leu Pro
                725                 730                 735

Pro Ser Arg Glu Glu Met Thr Lys Asn Gln Val Ser Leu Thr Cys Leu
            740                 745                 750

Val Lys Gly Phe Tyr Pro Ser Asp Ile Ala Val Glu Trp Glu Ser Asn
        755                 760                 765

Gly Gln Pro Glu Asn Asn Tyr Lys Thr Thr Pro Pro Val Leu Asp Ser
    770                 775                 780

Asp Gly Ser Phe Phe Leu Tyr Ser Lys Leu Thr Val Asp Lys Ser Arg
785                 790                 795                 800

Trp Gln Gln Gly Asn Val Phe Ser Cys Ser Val Met His Glu Ala Leu
                805                 810                 815

His Asn His Tyr Thr Gln Lys Ser Leu Ser Leu Ser Pro Gly Lys
            820                 825                 830


<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Val Glu Val Asp
1


<210> SEQ ID NO 6
<211> LENGTH: 20
<212> TYPE: PRT
<213> ORGANISM: Artificial Sequence
<220> FEATURE:
<223> OTHER INFORMATION: Synthetic

<400> SEQUENCE: 6

Met Tyr Arg Met Gln Leu Leu Ser Cys Ile Ala Leu Ser Leu Ala Leu
1               5                   10                  15

Val Thr Asn Ser
            20
```

HUMANIZED ACE2-Fc FUSION PROTEIN FOR TREATMENT AND PREVENTION OF SARS-CoV-2 INFECTION

CROSS REFERENCE TO RELATED APPLICATIONS

The present application is a United States National Phase under 35 U.S.C. § 371 of International Application No. PCT/US2021/037344, filed Jun. 15, 2021, which claims the benefit of the filing date of U.S. Provisional Application No. 63/039,228, filed Jun. 15, 2020, the entire contents of both of which are incorporated by reference herein in their entirety.

REFERENCE TO SEQUENCE LISTING

The application contains a Sequence Listing that has been filed electronically in the form of a text file, created Dec. 15, 2022, and named "112969-0059-7000US00_SEQ.TXT" (22,068 bytes), the contents of which are incorporated by reference herein in their entirety.

BACKGROUND OF THE INVENTION

A novel coronavirus was first reported in Wuhan City, Hubei Province, China and later named severe acute respiratory syndrome coronavirus 2 (SARS-CoV-2). Guan et al, 2020; *N Engl J Med* 382: 1708-1720 and Huang et al, 2021; *EMBO Mol Med* 13: e12828. Coronaviruses are a family of RNA viruses that have been previously identified as having six subtypes, with SARS-CoV-2 now classified as the seventh. Four of the six subtypes are less pathogenic and usually result in mild catarrhal presentation after infection whereas two previously identified viral subtypes, known as the viruses causing SARS-CoV and Middle East Respiratory Syndrome (MERS), have rapid transmission rates. Wong et al, *Cell Host Microbe* 2015; 18(4):398-401. SARS-CoV-2 spreads more efficiently than SARS-CoV in 2003 and MERS-CoV in 2015 and causes the disease, named coronavirus disease 2019 (COVID-19). Infection with SARS-CoV-2 results in atypical pneumonia with symptoms including fever, coughing, fatigue, and breathing difficulties. There is a need to develop new therapies for the treatment of SARS-CoV-2 infection.

SUMMARY OF THE INVENTION

The present disclosure is based, at least in part, on the development of superior decoy fusion proteins having high binding affinity and specificity to SARS-CoV-2 spike protein S. In some cases, the decoy fusion protein binds to a receptor binding domain (RBD) of S1. In other examples, the decoy fusion protein binds to a region outside the RBD. The decoy fusion proteins disclosed herein showed ability to block the binding of spike protein S to the angiotensin-converting enzyme 2 (ACE2) receptor, which in turn may inhibit the ability of SARS-CoV-2 to effectively infect cells (e.g., human cells). Accordingly, the decoy fusion protein disclosed here are expected to be effective in blocking entry of SARS-CoV2 in to host cells, thereby inhibiting SARS-CoV2 infection of hosts such as human subjects.

Accordingly, the present disclosure provides, in some aspect, a fusion polypeptide that binds the spike protein of a coronavirus (e.g., SARS such as SARS-CoV-2). The fusion polypeptide may comprise a fragment of an angiotensin-converting enzyme 2 (ACE2) receptor (e.g., a human ACE2 receptor) and an Fc region of an immunoglobulin. Such a fusion polypeptide binds the coronavirus and suppresses its entry into host cells via the ACE2 receptor.

In some embodiments, the fragment of the ACE2 receptor may comprise at least one binding site for a spike protein of the coronavirus. In some embodiments, the fragment of the ACE2 receptor may comprise the ectodomain of the ACE2 receptor. In some examples, the fragment of the ACE2 receptor may comprise an amino acid sequence at least 90% (e.g., at least 95%, at least 97%, at least 98%, or at least 99%) identical to SEQ ID NO:2. In one specific example, the fragment of the ACE2 receptor comprises the amino acid sequence of SEQ ID NO:2.

Alternatively or in addition, the Fc region in any of the fusion polypeptide disclosed herein may be of an immunoglobulin, which can be a human IgG1 molecule, a human IgG2, a human IgG3, or a human IgG4 molecule. In some examples, the Fc region is of human IgG1. In other examples, the Fc region is of human IgG4. In some instances, the Fc region in the fusion polypeptide may comprise an amino acid sequence at least 90% (e.g., at least 95%, at least 97%, at least 98%, or at least 99%) identical to SEQ ID NO:3. In one example, the Fc region in the fusion polypeptide comprises the amino acid sequence of SEQ ID NO:3.

In some embodiments, the fragment of the ACE receptor and the Fc fragment can be linked via a peptide linker, for example, VEVD (SEQ ID NO: 5).

In some embodiments, a fusion polypeptide disclosed herein may further include a signaling peptide at the C-terminus. In some example, the fusion polypeptide disclosed herein may encompass an amino acid sequence at least 90% (e.g., at least 95%, at least 97%, at least 98%, or at least 99%) identical to SEQ ID NO: 4. In one specific example, the fusion polypeptide disclosed herein comprises the amino acid sequence of SEQ ID NO:4.

Any of the ACE2-Fc fusion polypeptide may be conjugated with a therapeutic agent, which may be a small molecule or a nucleic acid.

In another aspect, provided herein is an isolated nucleic acid, which comprises a nucleotide sequence encoding any of the fusion polypeptides disclosed herein (e.g., the fusion polypeptide of SEQ ID NO:7). Such a nucleic acid may be a vector, for example, an expression vector. Also provided herein is a host cell comprising any of the nucleic acids disclosed herein that encodes the fusion polypeptide. Such a host cell may be a bacterial cell, a yeast cell, an insect cell, or a mammalian cell.

In yet another aspect, the present disclosure features a pharmaceutical composition comprising any of the fusion polypeptides disclosed herein or its encoding nucleic acid and a pharmaceutically acceptable carrier.

In addition, the present disclosure provides a method for treating or inhibiting a coronavirus infection in a subject. The method may comprise administering to the subject in need thereof an effective amount of any of the fusion polypeptides disclosed herein, the encoding nucleic acids, or the pharmaceutical composition comprising such. The subject may have, may be suspected of having, or may be at risk of having, a disease associated with a coronavirus infection. The disease may be an infection caused by SARS, for example, SARS-CoV-2. In one example, the disease may be COVID-19.

Also within the scope of the present disclosure are any of the fusion polypeptides, nucleic acids encoding such, or pharmaceutical compositions comprising such as disclosed herein for use in treating a disease caused by a coronavirus infection, such as those described herein, as well as use of any of the fusion polypeptides or encoding nucleic acids disclosed herein for manufacturing a medicament for use in treating any of the target diseases as also disclosed herein.

Further, the present disclosure provides a method for producing an ACE2-Fc fusion polypeptide as disclosed herein, the method comprising: (i) culturing host cells comprising a nucleic acid encoding the fusion polypeptide under conditions allowing for expressing of the fusion polypeptide; and (ii) harvesting the fusion polypeptide thus produced.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to the drawing in combination with the detailed description of specific embodiments presented herein.

FIG. 1A: Schematic illustrations of various SARS-CoV-2 Spike fragments and ACE constructions. FIG. 1B: Western blot analysis of SARS-CoV-2 Spike 1-1273 (full length), 1-674 (S1), and 319-591 (RBD-SD1) fragments. FIG. 1C: Purity and molecular size analysis of ACE2-Fc by Coomassie Brilliant Blue staining using reducing or non-reducing loading dye. FIG. 1D: Formation of homodimers by purified ACE2-Fc fusion polypeptide as observed in non-reducing sodium dodecyl sulfate-polyacrylamide gel electrophoresis. FIG. 1E: Detection of homodimers formed by ACE2-Fc fusion polypeptide and Spike S1-Fc fusion polypeptide in nonreducing Coomassie Brilliant Blue staining. FIG. 1F: Glycosylation of ACE2-Fc and Spike 1-674-Fc fusion polypeptides as observed in a PNGase F assay. PNGase F digested ACE2-Fc (500 ng) and Spike 1-674-Fc (500 ng) and the deglycosylated products were observed by Coomassie Brilliant Blue staining.

FIG. 2A: a chart showing peptidase activity of ACE2-Fc. The peptidase activity of ACE2-Fc was measured by cleavage of fluorescent peptide substrates. FIG. 2B: a diagram showing inhibition of angiotensin II (Ang II)-induced TNF-α production by ACE2-Fc. Ang II was pre-incubated with indicated amounts of ACE2-Fc or IgG for 30 min. After that, the mixtures were added to RAW264.7 cells for 12 h. The concentration of TNF-a in the culture medium was determined by ELISA. Error bars represent the standard deviation (SD), n=3. Statistical analysis was performed by unpaired two-tail t-test. *P<0.05. The dotted line represents the mean value of TNF-α in control group. FIG. 2C: a photo showing inhibition of Ang II-induced ADAM17 (a disintegrin and metalloprotease 17) phosphorylation by ACE2-Fc as observed in an immunoblotting analysis using the indicated antibodies. β-actin served as the loading control. FIG. 2D: a diagram obtained by normalizing the signal intensity in FIG. 2C to cells only. Data are representative of three independent experiments, and the values are expressed as the mean±SD. Error bars represent the standard deviation (SD), n=2. Statistical analysis was performed by unpaired two-tail t-test. *P<0.05. IgG represents the human normal IgG control.

FIG. 3A: a diagram showing the purity of biotin-conjugated ACE2-Fc fusion polypeptide or Fc control via immunoblotting with an anti-human IgG Fc antibody. IB: immunoblotting. IB: immunoblotted with indicated antibodies. FIG. 3B: an ELISA binding curve of ACE2-Fc to Spike 1-674 (S1). FIG. 3C: an ELISA binding curve of ACE2-Fc to Spike 319-591 (RBD-SD1). D: receptor binding domain; SD: connector domain. FIG. 3D: a diagram showing competition binding of ACE2-Fc to Spike S1 in the presence of excess ACE2-Fc using an ELISA assay. NTD: N-terminal domain; RBD: receptor binding domain; SD: connector domain; TM: transmembrane domain; CT: C-terminal tail; RFU: relative fluorescent unit. IB, immunoblotted with indicated antibodies. GAPDH is served as a loading control. FIG. 3E: a diagram showing competition binding of ACE2-Fc to soluble S1 protein in the presence of excess ACE2-Fc via an ELISA assay. NTD: N-terminal domain; RBD: receptor binding domain; SD: connector domain; TM: transmembrane domain; CT: C-terminal tail; RFU: relative fluorescent unit. IB, immunoblotted with indicated antibodies. GAPDH is served as a loading control.

FIG. 4A: a diagram showing expression of ACE2 in HEK293 and H1975 cells. The cells were transduced with full-length ACE2 by lentivirus. Protein extracts were immunoblotted with the indicated antibodies. 0/E represents overexpression. FIG. 4B: a schematic diagram for cell-cell fusion and syncytia formation. FIG. 4C: a diagram showing inhibition of cell-cell fusion by ACE2-Fc in HEK293/ACE2 and H1975/ACE2 cells. FIG. 4D: a diagram showing inhibition of syncytia formation by ACE2-Fc in HEK293/ACE2 and H1975/ACE2 cells. Error bars represent the standard deviation (SD), n=6. Statistical analysis was performed by unpaired two-tail t-test. P<0.01, *P<0.001.

FIG. 5A: a diagram showing viability of normal bronchial epithelia (NBE) in the presence of ACE2-Fc and normal human IgG at the indicated concentrations for 72 h as determined by MTS assay. Error bars represent the standard deviation (SD), n=2 in left; n=3 in right. The dotted line represents the 50% of cell viability. FIG. 5B: a diagram showing viability of human bronchial/tracheal epithelia cells in the presence of ACE2-Fc and normal human IgG at the indicated concentrations for 72 h as determined by MTS assay. Error bars represent the standard deviation (SD), n=2 in left; n=3 in right. The dotted line represents the 50% of cell viability. FIG. 5C: a diagram showing in vitro serum stability of ACE2-Fc. ACE2-Fc was incubated with 50% normal human serum at 37° C. for up to 10 days. At the indicated time points, samples were collected to quantify the binding ability of ACE2-Fc to Spike proteins by ELISA. Error bars represent the standard deviation (SD), n=3. Experiments were performed at least three times with similar results.

FIG. 6A: a diagram showing that ACE2-Fc blocked the entry of Spike-expressing pseudotyped lentivirus into HEK293T-ACE2 and H1975-ACE2 cells. The relative luciferase activities, normalized to the only virus group, represent the efficiency of virus entry. MOI: Multiplicity of infection. FIG. 6B: a diagram showing that ACE2-Fc fusion polypeptide blocked viral entry at a higher virus input. ACE2-Fc blocked Spike-expressing pseudotyped lentivirus entry into HEK293T-ACE2 and H1975-ACE2 cells. MOI (multiplicity of infection)=1. Virus entry was determined by measuring luciferase activity. R.I.U=relative infection unit. Error bars represent the standard deviation (SD), n=3. Statistical analysis was performed by unpaired two-tail t-test. *P<0.05, P<0.01, *P<0.001. FIG. 6C: a photo showing immunoblotting assays of lung cancer A549 cells, human normal bronchial epithelial cells (HBEpc), and HBEpc-differentiated cells (airway organoids) with the indicated antibodies. FIG. 6D: a diagram showing blockage of pseudovirus entry into airway organoids by ACE2-Fc. Mixtures of pseudotyped lentivirus with or without ACE2-Fc were cocultured with airway organoids for 72 h. The virus entry was determined by quantifying the luciferase activity in the cell lysates. Data information: Error bars represent the standard deviation (SD), n=3. Statistical analysis was performed by unpaired two-tail t-test. *P<0.05, P<0.01, *P<0.001. Experiments were performed at least three times with similar results.

FIG. 7A: a diagram showing inhibition of SARS-CoV-2 infection by ACE2-Fc in a plaque assay. Mixtures of ACE2-Fc and SARS-CoV-2 were incubated for 1 h before adding to Vero E6 cells for another 1 h at 37° C. The ACE2-Fc and SARS-CoV-2 pre-mixtures were removed, and the cells were washed once with PBS and overlaid with methylcellulose with 2% FBS for 5-7 days before being stained with crystal violet. Those results showed increase of plaque formation was regarded as no inhibition of plaque formation. TPCK-treated trypsin: N-tosyl-L-phenylalanine chloromethyl ketone-treated trypsin. FIG. 7B: a photo showing inhibitory effects of ACE2-Fc on protein expression by a yield reduction assay. The culture medium and cell extracts were harvested 24 h postinfection for Western blot. The NP/PCNA represents the relative NP expression as compared to that of PCNA, which served as a loading control. The NP/PCNA numbers below the panel are the ratios of NP/PCNA normalized to that of the human IgG control group. PCNA: Proliferating cell nuclear antigen. FIG. 7C: a diagram showing inhibitory effects of ACE2-Fc on virus titer by a yield reduction assay using real-time PCR.

FIG. 7D: Schematic illustration of the ACE2-Fc pretreatment and full-time experiment procedure, delineating the stages where the ACE2-Fc was present during the experiment. FIG. 7E: a photo showing immunoblotting assay of cell lysates from the pretreatment and full-time experiments with the indicated antibodies. FIG. 7F: a diagram showing SARS-CoV-2 titers in the pretreatment and full-time experiments, which were analyzed by real-time PCR. Data information: Error bars represent the standard deviation (SD), n=3. Statistical analysis was performed by unpaired two-tail t-test. *P<0.05, **P<0.01.

FIG. 8A: Yield reduction assay was performed to determine the inhibitory effects of ACE2-Fc on the entry of 5 different SARS-CoV-2 strains into Vero E6 cells. The NP proteins in the cell lysates were determined by Western blot analysis. FIG. 8B: The virus RNA in the culture medium was quantified by real-time RT-PCR. Error bars represent the standard deviation (SD), n=3. Statistical analysis was performed by unpaired two tail t-test. P<0.01, *P<0.001. Experiments were performed at least three times with similar results. FIG. 8C: The virus RNA in the cell lysates was quantified by real-time RT-PCR. Error bars represent the standard deviation (SD), n=3. Statistical analysis was performed by unpaired two tail t-test. P<0.01, *P<0.001. Experiments were performed at least three times with similar results.

FIG. 9A: a photo showing expression of Spike protein in H1975 cells transduced with full-length Spike by a lentiviral vector by immunoblotting with the indicated antibodies. 0/E represents overexpress. FIG. 9B: a diagram showing the effect of ACE2-Fc activation on degranulative capacity of NK cells as determined by the CD107a, IFN-γ, and TNF-α expression levels. The experiments were performed with the primary human NK cells derived from three independent donors. Error bars represent the standard deviation (SD), n=3. Statistical analysis was performed by unpaired two-tail t-test. *P<0.05 (each concentration of ACE2-Fc vs. control). FIGS. 9C-9E: diagrams showing the expression levels of CD107a (9A), IFN-γ (9B), and TNF-α (9C) as determined by flow cytometry after the NK cells and H1975-Spike cells co-incubation in the presence or absence of ACE2-Fc or ACE2 control. Error bars represent the standard deviation (SD), n=3. Statistical analysis was performed by unpaired two-tail t-test. *P<0.05. The percentage of positive cells in both groups was normalized to the NK/H1975-Spike only group.

DETAILED DESCRIPTION OF THE INVENTION

Figure 1A:
FIGS. 1A-1F include diagrams depicting the production and functional assessment of ACE2-Fc fusion protein.

Coronavirus such as SARS (e.g., SARS-CoV-2) infection is mediated by the transmembrane glycoprotein, Spike, which recognizes and targets angiotensin-converting enzyme 2 (ACE2) for viral entry (Zhou et al, 2020; *Nature* 579: 270-273). ACE2 is expressed on the cell membrane of most organs and tissues, including lungs, heart, kidney, brain, intestine and endothelial cells (Kabbani & Olds, 2020; *Mol Pharmacol* 97: 351-353). The viral Spike protein can be divided into two functionally distinct subunits, a receptor binding subunit S1 and a membrane-fusion subunit S2. The S1 subunit recognizes and binds to ACE2 on the host cells, while the fusiogenic peptide on S2 subunit facilitates the fusion between viral and host membrane to allow the release of viral genome into the host cell (Tortorici & Veesler, 2019; *Adv Virus Res* 105: 93-116). Based on the viral sequence alignment (Lu et al, 2020) as well as the Cryo-EM structure of SARS-CoV-2 Spike protein (Wrapp et al, 2020; *Science* 367: 1260-1263), high similarities between the Spike protein of SARS-CoV and SARS-CoV-2 have been described (Monteil et al, 2020; *Cell* 181: 905-913 e907). Recently, it was reported that the receptor binding domain (RBD) of SARS-CoV-2 S1 interacts with the peptidase domain (PD) of ACE2 (Li et al, 2005; *Science* 309: 1864-1868 and Wrapp et al., 2020; *Science* 367: 1260-1263).

As a component in the signaling pathway of the renin-angiotensin system (RAS), which functions as a homeostatic regulator of vascular function, ACE2 plays an important role in the maturation of angiotensin (Ang), which controls vasoconstriction and blood pressure (Patel et al, 2016*; Circ Res* 118: 1313-1326) as well as the inflammatory cytokine cascade mediated by TNF-α and IL-6 (Hirano T et al, 2020). ACE first metabolizes Ang I to Ang II, whose C-terminal domain is further cleaved by ACE2 to generate angiotensin 1-7 (Ang 1-7). Ang 1-7, having an opposing function to Ang II, has anti-oxidant and anti-inflammatory effects to lung and heart injury (Patel et al., 2016). The concentration of Ang II is delicately regulated. Increased levels of Ang II is believed to upregulate ACE2 activity, which then subsequently lead to decreased Ang II and increased Ang 1-7 levels. Treatment with recombinant human ACE2 (rhACE2) and B38-CAP, a bacteria-derived ACE2-like enzyme, has been reported to suppress Ang II-induced hypertension, cardiac hypertrophy, and fibrosis in the mouse model (Liu et al, 2018; Minato et al, 2020). Besides, ACE2 was shown to improve the sepsis-induced acute lung injury using caecal ligation and perforation (CLP) and endotoxin challenge (Imai et al, 2005*; Nature* 436: 112-116). In addition, impaired ACE2 expression was observed in mice receiving SARS-CoV Spike protein injection suggesting that the Spike proteins might worsen lung injury by hijack ACE2 function and its expression levels (Kuba et al, 2005*; Nat Med* 11: 875-879). It thus seems that ACE2 plays a key role in the cellular entry of SARS-CoV2 in addition to protect organs from injury.

Coronavirus infection is mediated by the transmembrane glycoprotein, S, which targets and binds to and uses ACE2 as its receptor for viral entry into the cell. Specifically, once the coronavirus binds to ACE2 through the S protein, fusion of the viral membrane and cell membrane occur. Subsequently, the virus will replicate its genome inside the cell, and ultimately make new virions that will be secreted to infect other cells.

SARS-CoV infection is mediated by the transmembrane glycoprotein, Spike, which recognizes and targets angiotensin-converting enzyme 2 (ACE2) for viral entry into the cell. ACE2 is a type I integral-membrane protein with an enzymatically active N-terminal ectodomain, a transmembrane region, and a short C-terminal cytoplasmic tail. The ectodomain of ACE2 (also referred to herein as the extracellular domain of ACE2) is cleaved from the transmembrane domain by another enzyme known as sheddase, and the resulting soluble protein is released into the blood stream and ultimately excreted into urine.

The present disclosure is based, at least in part, on the development of a decoy ACE2-Fc fusion protein capable of blocking entry of coronavirus into host cells via the ACE2 receptor. Such a decoy protein comprises (a) an ACE2 receptor or a fragment thereof capable of binding to a Spike protein of a coronavirus (e.g., the Spike protein of SARS-CoV2), and (b) an Fc fragment of an immunoglobulin molecule. The decoy fusion proteins herein prevent a coronavirus from fusing with the cell membrane by specifically binding the Spike protein with high affinity over endogenous ACE2. Accordingly, provided herein are decoy ACE2-Fc fusions proteins and uses thereof in inhibiting and/or treating coronavirus infection.

I. Decoy ACE2-Fc Fusion Proteins Binding to Coronavirus Spike Protein

In some aspects, the present disclosure provide decoy ACE2-Fc fusion proteins capable of binding to a spike protein of a coronavirus, such as the SARS-CoV-2 spike protein S. Decoy fusion proteins, such as those described herein, have a higher affinity and/or abundance for the viral spike protein then the native ACE2 receptor of the virus. As such, the decoy protein can reduce or prevent the coronavirus (via its Spike protein) from binding to the ACE2 receptors on host cells for infection.

In some embodiments, the decoy fusion proteins disclosed herein are capable of binding to the S1 subunit of SARS-CoV-2 spike protein S. In some embodiments, the decoy fusion proteins disclosed herein are capable of binding to the receptor binding domain (RBD).

As such, the decoy fusion proteins disclosed herein may be used for either therapeutic or diagnostic purposes to prevent, treat or diagnose an infection caused by a coronavirus (e.g., SARS such as SARS-CoV-2). In some instances, the decoy protein can be used for treating COVID-19.

Any of the decoy ACE2-Fc fusion proteins described herein can inhibit (e.g., reduce or eliminate) the ability of a coronavirus such as SARS (e.g., SARS-CoV-2) to enter into host cells (e.g., $ACE2^+$ human cells) and undergo viral replication therein. In some embodiments, the decoy ACE2-Fc fusion proteins as described herein can inhibit viral replication (e.g., replication of SARS-CoV-2) by at least 30% (e.g., 35%, 40%, 45%, 50%, 60%, 70%, 80%, 90%, 95% or greater, including any increment therein). The inhibitory activity of decoy fusion proteins on SARS-CoV-2 replication described herein can be determined by routine methods known in the art, e.g., by an assay for measuring the percentage inhibition of virus yield.

In some examples, the percentage inhibition of virus yield by a decoy ACE2-Fc fusion protein may be calculated as:

$$\left[1-\left(\frac{Vd}{Vc}\right)\right]\times 100\%, \quad \text{(Equation 1)}$$

in which Vd and Vc refer to the virus copies in the in the presence and absence of the test compound. In some embodiments, the decoy fusion protein described herein. Any of the decoy fusion proteins as described herein, e.g., the exemplary ACE2-Fc decoy fusion proteins provided herein, may result in a 30%, 35%, 40%, 45%, 50%, 60%, 70%, 80%, 90%, 95%, or greater percentage inhibition of SARS-CoV-2 virus yield.

(A) ACE2-Fc Decoy Fusion Proteins

In one aspect, the present disclosure provides ACE2-Fc decoy fusion proteins having at least one binding site of an ACE2 receptor for a spike protein of a coronavirus. In some embodiments, an ACE2 decoy fusion protein herein encompasses a full length human ACE2 (SEQ ID NO: 1). In other embodiments, an ACE2 decoy fusion protein herein encompasses a fragment of human ACE2 that contains at least one binding site to a spike protein of a coronavirus. A fragment of ACE2 may include the complete ectodomain (SEQ ID NO: 2), a portion of the ectodomain, the complete transmembrane domain, a portion of the transmembrane domain, the complete cytoplasmic tail, a portion of the cytoplasmic tail, or a combination thereof.

In some embodiments, an ACE2 decoy fusion protein disclosed herein encompasses an ACE2 ectodomain domain or a fragment thereof comprising at least one binding site to a spike protein of a coronavirus. In some examples, an ACE2 decoy fusion protein herein encompasses at least one binding site for the subunit S1 of the spike protein of a coronavirus. In another example, an ACE2 decoy fusion protein herein encompasses at least one binding site for RBD of the spike protein of a coronavirus.

In some embodiments, an ACE2 fusion protein can include an ectodomain domain of an ACE2 and/or one of its active fragments and further comprises a fusion partner (e.g., Fc) comprising a dimerization domain as well as an ACE2 ectodomain domain. When the fusion partner comprises a dimerization domain, such as an Fc domain or an active fragment thereof, the ACE2 decoy fusion protein expressed in a mammalian cell expression system may naturally form a dimer during the production process. In other examples, an ACE2 decoy fusion protein disclosed herein can form stable homodimer. In some examples, an ACE2 decoy fusion protein herein can be engineered to artificially form stable homodimer. In some embodiments, the decoy fusion proteins disclosed herein may include a human ACE polypeptide having residues 18 to 615. In some embodiments, the decoy fusion proteins disclosed herein may comprise ACE polypeptide having a sequence of any of the proteins in Table 1 below.

In some embodiments, the decoy fusion proteins disclosed herein may comprise an ACE polypeptide that is at least 80% (e.g., 85%, 90%, 95%, or 98%) sequence identity as compared with SEQ ID NO: 1 or SEQ ID NO: 2. The "percent identity" of two amino acid sequences is determined using the algorithm of Karlin and Altschul, *Proc Natl Acad Sci* USA 87:2264-68, 1990, modified as in Karlin and Altschul, *Proc Natl Acad Sci* USA 90:5873-77, 1993. Such an algorithm is incorporated into the NBLAST and XBLAST programs (version 2.0) of Altschul et al. *J Mol Biol* 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res* 25(17):3389-3402, 1997. When utilizing BLAST and Gapped BLAST programs, the default parameters of the respective programs (e.g., XBLAST and NBLAST) can be used.

In some instances, the ACE2 portion in any of the ACE-Fc fusion polypeptides disclosed herein may comprise one or more conservative amino acid residues as compared to a reference sequence, for example, SEQ ID NO:1 or SEQ ID NO:2. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

TABLE 1

Sequences of Human ACE2 Receptor

| Protein | Amino Acid Sequence | SEQ ID NO: |
|---|---|---|
| Full length Human ACE2 | MSSSSWLLLSLVAVTAAQSTIEEQAKTFLDKFNHEAEDLFYQSSLA<br>SWNYNTNITEENVQNMNNAGDKWSAFLKEQSTLAQMYPLQEIQNLT<br>VKLQLQALQQNGSSVLSEDKSKRLNTILNTMSTIYSTGKVCNPDNP<br>QECLLLEPGLNEIMANSLDYNERLWAWESWRSEVGKQLRPLYEEYV<br>VLKNEMARANHYEDYGDYWRGDYEVNGVDGYDYSRGQLIEDVEHTF<br>EEIKPLYEHLHAYVRAKLMNAYPSYISPIGCLPAHLLGDMWGRFWT<br>NLYSLTVPFGQKPNIDVTDAMVDQAWDAQRIFKEAEKFFVSVGLPN<br>MTQGFWENSMLTDPGNVQKAVCHPTAWDLGKGDFRILMCTKVTMDD<br>FLTAHHEMGHIQYDMAYAAQPFLLRNGANEGFHEAVGEIMSLSAAT<br>PKHLKSIGLLSPDFQEDNETEINFLLKQALTIVGTLPFTYMLEKWR<br>WMVFKGEIPKDQWMKKWWEMKREIVGVVEPVPHDETYCDPASLFHV<br>SNDYSFIRYYTRTLYQFQFQEALCQAAKHEGPLHKCDISNSTEAGQ<br>KLFNMLRLGKSEPWTLALENVVGAKNMNVRPLLNYFEPLFTWLKDQ<br>NKNSFVGWSTDWSPYADQSIKVRISLKSALGDKAYEWNDNEMYLFR<br>SSVAYAMRQYFLKVKNQMILFGEEDVRVANLKPRISFNFFVTAPKN<br>VSDIIPRTEVEKAIRMSRSRINDAFRLNDNSLEFLGIQPTLGPPNQ<br>PPVSIWLIVFGVVMGVIVVGIVILIFTGIRDRKKKNKARSGENPYA<br>SIDISKGENNPGFQNTDDVQTSF | 1 |
| Ectodomain of human ACE2 | QSTIEEQAKTFLDKFNHEAEDLFYQSSLASWNYNTNITEENVQNMN<br>NAGDKWSAFLKEQSTLAQMYPLQEIQNLTVKLQLQALQQNGSSVLS<br>EDKSKRLNTILNTMSTIYSTGKVCNPDNPQECLLLEPGLNEIMANS<br>LDYNERLWAWESWRSEVGKQLRPLYEEYVVLKNEMARANHYEDYGD<br>YWRGDYEVNGVDGYDYSRGQLIEDVEHTFEEIKPLYEHLHAYVRAK<br>LMNAYPSYISPIGCLPAHLLGDMWGRFWTNLYSLTVPFGQKPNIDV<br>TDAMVDQAWDAQRIFKEAEKFFVSVGLPNMTQGFWENSMLTDPGNV<br>QKAVCHPTAWDLGKGDFRILMCTKVTMDDFLTAHHEMGHIQYDMAY<br>AAQPFLLRNGANEGFHEAVGEIMSLSAATPKHLKSIGLLSPDFQED<br>NETEINFLLKQALTIVGTLPFTYMLEKWRWMVFKGEIPKDQWMKKW<br>WEMKREIVGVVEPVPHDETYCDPASLFHVSNDYSFIRYYTRTLYQF<br>QFQEALCQAAKHEGPLHKCDISNSTEAGQKLFNMLRLGKSEPWTLA<br>LENVVGAKNMNVRPLLNYFEPLFTWLKDQNKNSFVGWSTDWSPYAD | 2 |

The present disclosure provides for decoy fusion proteins that may optionally include an Fc fragment of an immunoglobulin molecule. In some embodiments, the decoy fusion protein is a humanized decoy fusion protein optimally including at least a portion of an immunoglobulin constant region or domain (Fc), typically that of a human immunoglobulin. Decoy fusion proteins may have Fc regions modified as described in WO 99/58572. Humanized decoy fusion proteins may also involve affinity maturation. Methods for constructing humanized decoy fusion proteins are also well known in the art. See, e.g., Rath et al., *Crit Rev Biotechnol.* 35(2):235-254 (2015).

In some embodiments, the human Fc domain fusion partner comprises the entire Fc domain. In some embodiments, the decoy fusion protein encompasses one or more fragments of the Fc domain. For example, the decoy fusion protein may include a hinge and the CH2 and CH3 constant domains of a human IgG, for example, human IgG1, IgG2, or IgG4. In some embodiments, decoy fusion protein disclosed herein encompasses a variant Fc polypeptide or a fragment of a variant Fc polypeptide. The variant Fc may comprise a hinge, CH2, and CH3 domains of human IgG. In an embodiment, a decoy fusion protein herein may be a homodimeric protein linked through at least one residue in the hinge region of an IgG Fc. An exemplary human Fc domain is:

```
                                       (SEQ ID NO: 3)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPGK
```

In some embodiments, the decoy fusion proteins disclosed herein may comprise a Fc domain that is at least 80% (e.g., 85%, 90%, 95%, or 98%) sequence identity as compared with SEQ ID NO: 3.

In some instances, the Fc fragment can be the Fc region of a wild-type IgG molecule. In other instances, the Fc fragment may comprise one or more mutations relative to a wild-type counterpart. Such mutations may lead to modified features, for example, improved stability (e.g., S228P substitution in an IgG4 Fc fragment) and/or modulated effector activity.

In some embodiments, an Fc domain can be linked to the N-terminus of a decoy protein fragment (e.g., ACE2 or a fragment of ACE2) or, alternatively, the decoy protein fragment can be linked to the N-terminus of the Fc domain. The Fc domain may comprise a linker, for example, a peptide linker, which may or may not comprise an enzyme cleavage site. A peptide linker may include at least 1 amino acid residue (natural or non-natural) between the Fc domain and decoy protein fragment. In some embodiments, a Fc domain and a decoy protein fragment are attached by an amino acid linker that is about 1 to about 10 amino acids in length. Alternatively, or in addition, other peptide and non-peptide linkers may also be used to link one or more of the Fc domains and decoy protein fragments disclosed herein. Exemplary amino acid linkers include AS and VEVD (SEQ ID NO: 5). In some embodiments, Fc domains herein may also comprise a molecule that extends the in vivo half-life by imparting improved receptor binding to the decoy protein fragment within an acidic intracellular compartment, for example, an acid endosome or a lysosome.

In some embodiments, a decoy fusion protein may optionally include a signal peptide. A signal peptide can enhance specificity of binding to a target protein, be used in decoy fusion protein generation and purification in culture medium. Signal peptides can be derived from antibodies, such as, but not limited to, CD8 or CD4, as well as epitope tags such as, but not limited to, GST or FLAG. In some embodiments, an IL-2 signal sequence (MYRMQLLSCIALSLALVTNS; SEQ ID NO: 6) can be located C-terminally of the decoy fusion protein. Other signal peptides may be used. In other embodiments, a decoy fusion protein may optionally include a cleavage site between a signal peptide and the C-terminus of the decoy fusion protein.

In an exemplary example, a decoy fusion polypeptide includes the ectodomain of human ACE2, optionally fused with an Fc region of human IgG1 at N-terminus and an IL-2 signaling peptide at C-terminus. In some examples, a peptide linker connects the Fc region of human IgG1 at the N-terminus to an ectodomain of human ACE2 and a peptide linker connects the IL-2 signaling peptide at C-terminus to the ectodomain of human ACE2. In an exemplary example, a mature decoy fusion polypeptide herein has an amino acid sequence as follows, where the linker is underlined and the Fc region is italicized:

(SEQ ID NO: 4)

<u>AS</u>QSTIEEQAKTFLDKFNHEAEDLFYQSSLASWNYNTNITEENVQNMNNAGDKWSAFLK

EQSTLAQMYPLQEIQNLTVKLQLQALQQNGSSVLSEDKSKRLNTILNTMSTIYSTGKVC

NPDNPQECLLLEPGLNEIMANSLDYNERLWAWESWRSEVGKQLRPLYEEYVVLKNEMAR

ANHYEDYGDYWRGDYEVNGVDGYDYSRGQLIEDVEHTFEEIKPLYEHLHAYVRAKLMNA

YPSYISPIGCLPAHLLGDMWGRFWTNLYSLTVPFGQKPNIDVTDAMVDQAWDAQRIFKE

AEKFFVSVGLPNMTQGFWENSMLTDPGNVQKAVCHPTAWDLGKGDFRILMCTKVTMDDF

LTAHHEMGHIQYDMAYAAQPFLLRNGANEGFHEAVGEIMSLSAATPKHLKSIGLLSPDF

QEDNETEINFLLKQALTIVGTLPFTYMLEKWRWMVFKGEIPKDQWMKKWWEMKREIVGV

VEPVPHDETYCDPASLFHVSNDYSFIRYYTRTLYQFQFQEALCQAAKHEGPLHKCDISN

STEAGQKLFNMLRLGKSEPWTLALENVVGAKNMNVRPLLNYFEPLFTWLKDQNKNSFVG

WSTDWSPYAD <u>VEVD</u>*DKTHTCPPCPAPELLGGPSVFLFPPKPKDTLMISRTPEVTCVVVD*

*VSHEDPEVKFNWYVDGVEVHNAKTKPREEQYNSTYRVVSVLTVLHQDWLNGKEYKCKVS*

*NKALPAPIEKTISKAKGQPREPQVYLPPPSREEMTKNQVSLTCLVKGFYPSDIAVEWES*

*NGQPENNYKTTPPVLDSDGSFFLYSKLTVDKSRWQQGNVFSCSVMHEALHNHYTQKSLS*

*LSPGK*

Also provided herein are ACE2-Fc fusion proteins comprising an amino acid sequence at least 80% (e.g., at least 85%, 90%, 95%, 97%, 98%, 99%, or higher) identical to SEQ ID NO:4.

Any of the ACE2-Fc fusion polypeptide disclosed herein may be conjugated with a therapeutic agent to form an antibody-drug conjugate like complex. In some instances, the therapeutic agent may be a small molecule (e.g., a small molecule anti-viral agent). In other instances, the therapeutic agent may be a nucleic acid-based agent (e.g., a nucleic acid-based anti-viral agent).

(B) Methods of Preparing Fusion Proteins

Any of the ACE2-Fc decoy fusion proteins disclosed herein can be made by any method known in the art. See, for example, Harlow and Lane, (1998) *Antibodies: A Laboratory Manual*, Cold Spring Harbor Laboratory, New York. In some embodiments, the antibody may be produced by the conventional hybridoma technology.

If desired, a decoy fusion protein of interest may be sequenced and the polynucleotide sequence may then be cloned into a vector for expression or propagation. The sequence encoding the decoy fusion protein of interest may be maintained in vector in a host cell and the host cell can then be expanded and frozen for future use. In an alternative, the polynucleotide sequence may be used for genetic manipulation to, e.g., humanize the decoy fusion protein or to improve the affinity (affinity maturation), or other characteristics of the decoy fusion protein. For example, the Fc region may be engineered to more resemble human Fc regions to avoid immune response if the decoy fusion protein is from a non-human source and is to be used in clinical trials and treatments in humans. Alternatively or in addition, it may be desirable to genetically manipulate the decoy fusion protein sequence to obtain greater affinity and/or specificity to the target protein and greater efficacy in binding to a spike protein of a coronavirus, thereby blocking entry of the virus into host cells via the ACE2 receptor. It will be apparent to one of skill in the art that one or more polynucleotide changes can be made to the decoy fusion protein and still maintain its binding specificity to the target protein.

Genetically engineered decoy fusion proteins, such as humanized decoy fusion proteins, chimeric decoy fusion proteins, and homodimer decoy fusion proteins can be produced via, e.g., conventional recombinant technology. In one example, DNA encoding a decoy fusion proteins specific to a target protein can be readily isolated and sequenced using conventional procedures (e.g., by using oligonucleotide probes that are capable of binding specifically to genes encoding the Fc and decoy protein fragment). Once isolated, the DNA may be placed into one or more expression vectors, which are then transfected into host cells such as *E. coli* cells, simian COS cells, Chinese hamster ovary (CHO) cells, Human Embryotic Kidney (HEK) 293 cells or myeloma cells that do not otherwise produce the decoy fusion proteins herein. The DNA can then be modified, for example, by substituting the coding sequence for human Fc domains in place of the homologous murine sequences, Morrison et al., (1984) *Proc Nat Acad Sci* 81:6851, or by covalently joining to the Fc coding sequence all or part of the coding sequence for a non-immunoglobulin polypeptide.

In some examples, decoy fusion proteins disclosed herein are prepared by recombinant technology as exemplified below.

Nucleic acids encoding the Fc and ACE2 decoy protein as described herein can be cloned into one expression vector, each nucleotide sequence being in operable linkage to a suitable promoter. In one example, each of the nucleotide sequences encoding the Fc and ACE2 decoy protein is in operable linkage to a distinct prompter. Alternatively, the nucleotide sequences encoding the Fc and ACE2 decoy protein can be in operable linkage with a single promoter, such that both the Fc and ACE2 decoy proteins are expressed from the same promoter. When necessary, an internal ribosomal entry site (IRES) can be inserted between the Fc and ACE2 decoy protein encoding sequences.

In some examples, the nucleotide sequences encoding at the Fc and ACE2 decoy proteins are cloned into two vectors, which can be introduced into the same or different cells. When the Fc and ACE2 decoy proteins are expressed in different cells, each of them can be isolated from the host cells expressing such and the isolated the Fc and ACE2 decoy proteins can be mixed and incubated under suitable conditions allowing for the formation of the Fc-ACE2 decoy protein homodimer.

Generally, a nucleic acid sequence encoding one or all proteins included in a decoy fusion protein disclosed herein can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the decoy fusion proteins.

A variety of promoters can be used for expression of the decoy fusion proteins described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., *Cell* 49:603-612 (1987)], those using the tetracycline repressor (tetR) [Gossen, M. and Bujard, H., *Proc Natl Acad Sci* USA 89:5547-5551 (1992); Yao, F. et al., *Human Gene Therapy,* 9:1939-1950 (1998); Shockelt, P., et al., *Proc. Natl. Acad. Sci. USA,* 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., *Cell,* 49:603-612 (1987); Gossen and Bujard (1992); M. Gossen et al., *Proc. Natl. Acad. Sci. USA,* 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., *Human Gene Therapy,* 10(16):1392-1399 (2003)). One particular advantage of this tetracycline inducible switch is that it does not require the use of a tetracycline repressor-mammalian cells transactivator or repressor fusion protein, which in some instances can be toxic to cells (Gossen et al., *Proc. Natl. Acad. Sci. USA,* 89:5547-5551 (1992); Shockett et al., *Proc. Natl. Acad. Sci. USA,* 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the decoy fusion proteins herein may be introduced into suitable host cells for producing the decoy fusion proteins. The host cells can be cultured under suitable conditions for expression of the decoy fusion protein or any polypeptide chain thereof. Such decoy fusion proteins or polypeptide chains thereof can be recovered by the cultured cells (e.g., from the cells or the culture supernatant) via a conventional method, e.g., affinity purification. If necessary, decoy fusion proteins can be incubated under suitable conditions for a suitable period of time allowing for production of the decoy fusion protein.

In some embodiments, methods for preparing a decoy fusion protein described herein involve a recombinant expression vector that encodes all components of the decoy fusion proteins as also described herein. The recombinant expression vector can be introduced into a suitable host cell (e.g., a HEK293T cell or a dhfr-CHO cell) by a conventional method, e.g., calcium phosphate-mediated transfection. Positive transformant host cells can be selected and cultured under suitable conditions allowing for the expression of the decoy fusion proteins which can be recovered from the cells or from the culture medium. When necessary, the decoy fusion proteins recovered from the host cells can be incubated under suitable conditions allowing for the formation of decoy fusion protein homodimers.

Standard molecular biology techniques are used to prepare the recombinant expression vector, transfect the host cells, select for transformants, culture the host cells and recovery of the decoy fusion proteins from the culture medium. For example, some decoy fusion proteins can be isolated by affinity chromatography with a Protein A or Protein G coupled matrix. In some examples, decoy fusion proteins herein may include a tag and the like to isolate and/or purify the decoy fusion protein. In other examples, decoy fusion proteins herein may be subjected to enzymatic cleavage to remove a tag, linker, signaling peptide, or a combination thereof after purification.

Any of the nucleic acids encoding the decoy fusion proteins as described herein, vectors (e.g., expression vectors) containing such; and host cells comprising the vectors are within the scope of the present disclosure.

II. Therapeutic Applications of Decoy Fusion Proteins

Any of the decoy fusion proteins disclosed herein can be used for therapeutic, diagnostic, and/or research purposes, all of which are within the scope of the present disclosure.

(A) Pharmaceutical Compositions

The decoy fusion proteins, as well as the encoding nucleic acids, vectors comprising such, or host cells comprising the vectors, as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some examples, the pharmaceutical composition described herein comprises liposomes containing the decoy fusion proteins (or the encoding nucleic acids) which can be prepared by methods known in the art, such as described in Epstein, et al., *Proc. Natl. Acad. Sci. USA* 82:3688 (1985); Hwang, et al., *Proc. Natl. Acad. Sci. USA* 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The decoy fusion proteins, or the encoding nucleic acid, may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic decoy fusion proteins compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing a decoy fusion protein with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

(B) Therapeutic Applications

To practice the method disclosed herein, an effective amount of the pharmaceutical composition described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. The subject may have, be at risk for, or be suspected of having, a target disease/disorder characterized by a coronavirus infection. The coronavirus may be SARS-CoV-2, severe acute respiratory syndrome coronavirus (SARS-CoV), or Middle East respiratory syndrome coronavirus (MERS-CoV). The coronavirus may also be human coronavirus 229E, NL63, OC43, or HKU1. In one example, the coronavirus is SARS-CoV-2. The target disease/disorder may be SARS, MERS, or COVID-19. In one example, the target disease/disorder is COVID-19.

A subject having a coronavirus infection or suspected of having the infection can be identified by routine medical examination, e.g., laboratory tests, organ functional tests, or CT scans. In one example, the subject has a SARS-CoV-2 infection or is suspected of having such an infection.

A subject suspected of having any of such target disease/disorder might show one or more symptoms of the disease/disorder. A subject at risk for the disease/disorder can be a subject having one or more of the risk factors for that disease/disorder.

As used herein, "an effective amount" refers to the amount of each active agent required to confer therapeutic effect on the subject, either alone or in combination with one or more other active agents. Determination of whether an amount of the decoy fusion protein achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, decoy fusion proteins that are compatible with the human immune system, such as humanized fusion proteins or fully human proteins, may be used to prolong half-life of the decoy fusion protein and to prevent the decoy fusion protein being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of a decoy fusion protein may be appropriate. Various formulations and devices for achieving sustained release are known in the art.

In one example, dosages for a decoy fusion protein as described herein may be determined empirically in individuals who have been given one or more administration(s) of the a decoy fusion protein. Individuals are given incremental dosages of the agonist. To assess efficacy of the agonist, an indicator of the disease/disorder can be followed.

Generally, for administration of any of the decoy fusion proteins described herein, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof.

An exemplary dosing regimen comprises administering an initial dose of about 2 mg/kg, followed by a weekly maintenance dose of about 1 mg/kg of the decoy fusion protein, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the decoy fusion protein used) can vary over time.

In some embodiments, for an adult patient of normal weight, doses ranging from about 0.3 to 5.00 mg/kg may be administered. In some examples, the dosage of the Fc-ACE2 decoy fusion protein described herein can be 10 mg/kg. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a decoy fusion protein as described herein will depend on the specific peptides (or compositions thereof) employed, the type and severity of the disease/disorder, whether the decoy fusion protein is administered for preventive or therapeutic purposes, previous therapy, the patient's clinical history and response to the agonist, and the discretion of the attending physician. Typically the clinician will administer a decoy fusion protein, until a dosage is reached that achieves the desired result. In some embodiments, the desired result is decrease or complete inhibition of coronavirus infection. In some examples, a decoy fusion protein can decrease the rate of coronavirus infection by at least 20% (e.g., 30%, 40%, 45%, 50%, 60%, 70%, 80%, 90%, 95% or greater, including any increment therein) following administration to a subject in need thereof. In some embodiments, the desired result is decrease or complete inhibition of coronavirus viral replication. In some examples, a decoy fusion protein can decrease the rate of coronavirus replication by at least 20% (e.g., 30%, 40%, 45%, 50%, 60%, 70%, 80%, 90%, 95% or greater, including any increment therein) following administration to a subject in need thereof. Methods of determining whether a dosage resulted in the desired result would be evident to one of skill in the art. Administration of one or more decoy fusion proteins can be continuous or intermittent, depending, for example, upon the recipient's physiological condition, whether the purpose of the administration is therapeutic or prophylactic, and other factors known to skilled practitioners. The administration of a decoy fusion protein may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity or prolonging survival. Alleviating the disease or prolonging survival does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble decoy fusion proteins can be administered by the drip method, whereby a pharmaceutical formulation containing the decoy fusion protein and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, a decoy fusion protein is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., *Trends Biotechnol.* (1993) 11:202; Chiou et al., Gene Therapeutics: Methods And Applications Of Direct Gene Transfer (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci. USA* (1990) 87:3655; Wu et al., *J. Biol. Chem.* (1991) 266:338.

Therapeutic compositions containing a polynucleotide (e.g., those encoding the antibodies described herein) are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem.* (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, *Mol. Cell. Biol.* (1994) 14:2411, and in Woffendin, *Proc. Natl. Acad. Sci.* (1994) 91:1581.

The particular dosage regimen, i.e., dose, timing and repetition, used in the method described herein will depend on the particular subject and that subject's medical history.

In some embodiments, more than one decoy fusion protein, or a combination of a decoy fusion protein and another suitable therapeutic agent, may be administered to a subject in need of the treatment. The decoy fusion protein can also be used in conjunction with other agents that serve to enhance and/or complement the effectiveness of the agents. For example, any of the ACE2-Fc decoy fusion protein may be co-used with one or more additional therapeutic agents for treating coronavirus infection (e.g., for treating COVID-19). Examples include remdesivir, an anti-SARS-CoV-2 antibody, or molnupiravir. Alternatively, the decoy fusion protein may be co-used with an anti-SARS-CoV-2 vaccine.

Treatment efficacy for a target disease/disorder can be assessed by methods well-known in the art.

III. Kits for Use in Inhibiting Coronavirus Infection

The present disclosure also provides kits for use in treating or alleviating a target disease, such as SARS infection (e.g., COVID-19) as described herein. Such kits can include one or more containers comprising a decoy fusion protein, e.g., any of those described herein. In some instances, the decoy fusion protein may be co-used with a second therapeutic agent.

In some embodiments, the kit can comprise instructions for use in accordance with any of the methods described herein. The included instructions can comprise a description of administration of the decoy fusion protein, and optionally the second therapeutic agent, to treat, delay the onset, or alleviate a target disease as those described herein. The kit may further comprise a description of selecting an individual suitable for treatment based on identifying whether that individual has the target disease, e.g., applying the diagnostic method as described herein. In still other embodiments, the instructions comprise a description of administering a decoy fusion protein to an individual at risk of the target disease.

The instructions relating to the use of a decoy fusion protein can generally include information as to dosage, dosing schedule, and route of administration for the intended treatment. The containers may be unit doses, bulk packages (e.g., multi-dose packages) or subunit doses. Instructions supplied in the kits of the invention are typically written instructions on a label or package insert (e.g., a paper sheet included in the kit), but machine-readable instructions (e.g., instructions carried on a magnetic or optical storage disk) are also acceptable. The label or package insert indicates that the composition is used for inhibiting SARS infection or treating COVID-19.

The kits disclosed herein are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a decoy fusion protein as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook, et al., 1989) Cold Spring Harbor Press; Oligonucleotide Synthesis (M. J. Gait, ed. 1984); Methods in Molecular Biology, Humana Press; Cell Biology: A Laboratory Notebook (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); DNA Cloning: A practical Approach, Volumes I and II (D. N. Glover ed. 1985); Nucleic Acid Hybridization (B. D. Hames & S. J. Higgins eds. (1985»; Transcription and Translation (B. D. Hames & S. J. Higgins, eds. (1984»; Animal Cell Culture (R. I. Freshney, ed. (1986»; Immobilized Cells and Enzymes (IRL Press, (1986»; and B. Perbal, A practical Guide To Molecular Cloning (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit, and scope of the present disclosure. All such modifications are intended to be within the scope of the disclosure.

Example 1. Production and Functional Analysis of ACE2-Fc Decoy Proteins

This example illustrates production and functional analysis of an exemplary ACE2-Fc decoy protein.

(i) Production of Recombinant Polypeptides

The 18-615 amino acid residues (the ectodomain) of ACE2 or 1-1,273, 1-674, and 319-591 amino acid residues of the SARS-CoV-2 Spike with humanized codons were PCR-amplified and cloned into pCDNA 3.1(−) plasmids with the Fc region of human IgG1 using Nhe I and Sal I restriction enzymes. Constructs of these protein fragments are illustrated in FIG. 1A. The ectodomain of human ACE2 (residues 18 to 615) was fused with an Fc region of human IgG1 at N-terminus via a peptide linker. The resultant fusion polypeptide also includes and IL-2 signaling peptide at the N-terminus to facilitate secretion of ACE2-Fc from the host cells producing such.

The Expi293F system (Thermo Fisher Scientific) was applied to generate recombinant proteins in the culture medium. According to the manufacturer's recommendation, Expi293F cells were maintained in Expi293 expression medium with a shaking speed of 120 rpm at 37° C. These soluble recombinant proteins were purified by Protein G Sepharose (Merck). The concentration of recombinant protein was measured at 280 nm by NanoDrop, and the purity was determined by polyacrylamide gel electrophoresis.

Western blotting was performed as previously described (Huang et al, 2016). In brief, total cell lysates were prepared in IP lysis buffer (20 mM Tris, pH 7.5, 100 mM sodium chloride, 1% IGEPAL CA-630, 100 μM $Na_3VO_4$, 50 mM NaF, and 30 mM sodium pyrophosphate) containing complete protease inhibitor cocktail without EDTA (Roche Diagnostics, Basel, Switzerland). Protein concentrations were measured by the Bio-Rad Protein Assay (Bio-Rad, Richmond, CA). The primary antibodies used at a 1:1,000 to 1:10,000 dilutions were as follows: anti-flag (M2, Sigma, 1:10,000); anti-ACE2 (ab108209, Abcam, 1:1,000); anti-TPMRSS2 (sc-515727, Santa Cruz, 1:1,000); anti-Spike (GTX632604, GeneTex, 1:1,000); anti-ADAM17 (T735, ab182630, Abcam, 1:1,000); anti-angiotensin II Type 1 Receptor antibody (ab124734, Abcam, 1:1,000); anti-GAPDH (10494-1-AP, Proteintech, 1:5,000); human FC (12136, Sigma, 1:10,000); NP: anti-nucleoprotein of SARS-CoV-2 (40143-R019, Sino biological, 1:5,000); and anti-PCNA (Millipore Corporation, 1:5,000). Horseradish peroxidase-conjugated anti-mouse (ab97023, Abcam, 1:5,000) and anti-rabbit (626520, Invitrogen, 1:5,000) secondary antibodies at the 1:5,000 dilution were used in the analysis. Alexa Fluor® 594 goat anti-mouse IgG (A11032, Thermo Fisher Scientific, 1:500) was used as the secondary antibody for the immunofluorescence experiment. Protein signals were detected by chemiluminescent reagent (NEL105001EA, PerkinElmer).

Figure 1B:
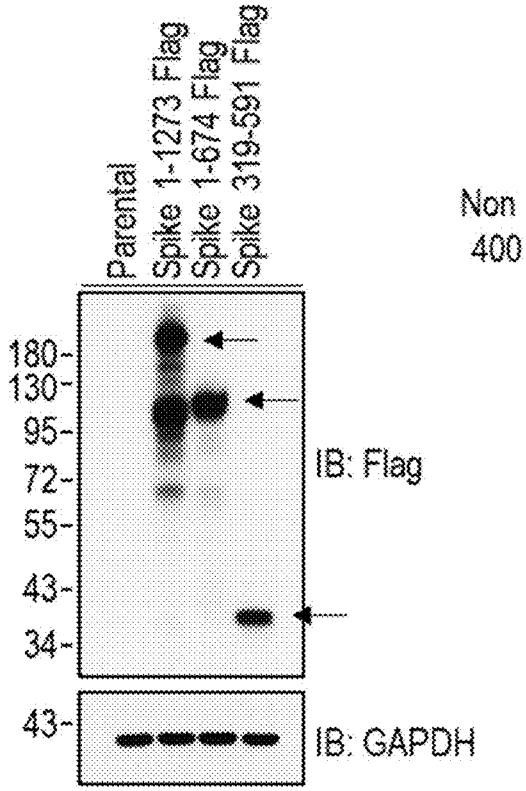

FIG. 1B shows a western blot analysis of SARS-CoV-2 Spike protein constructs: 1-1273 (full length), 1-674 (S1), and 319-591 (RBD-SD1) amino acid.

Figure 1C:
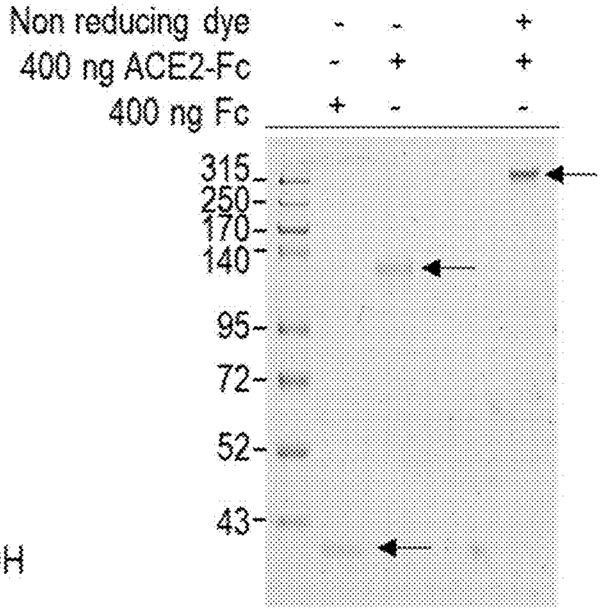
Figure 1D:
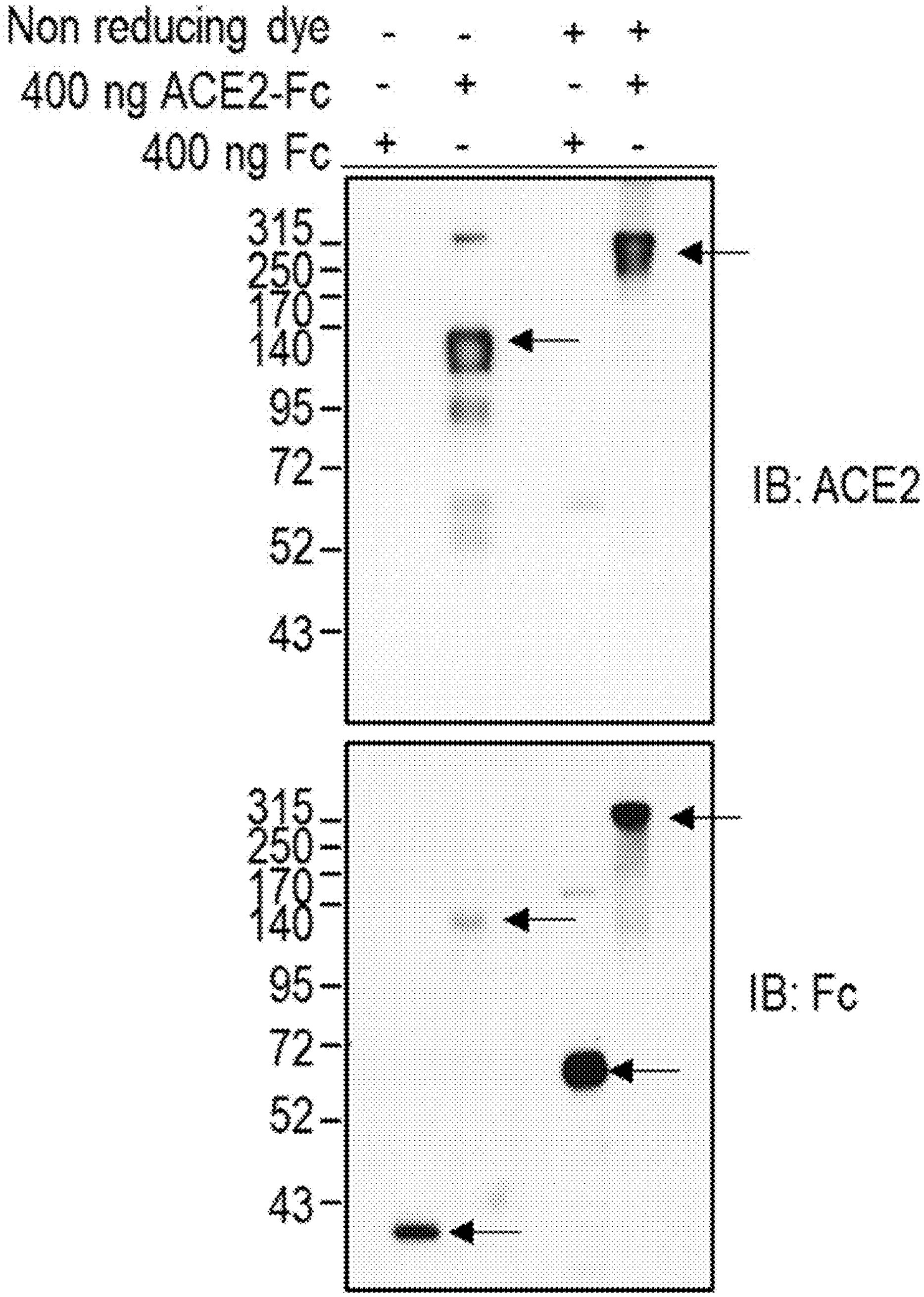
Figure 1E:
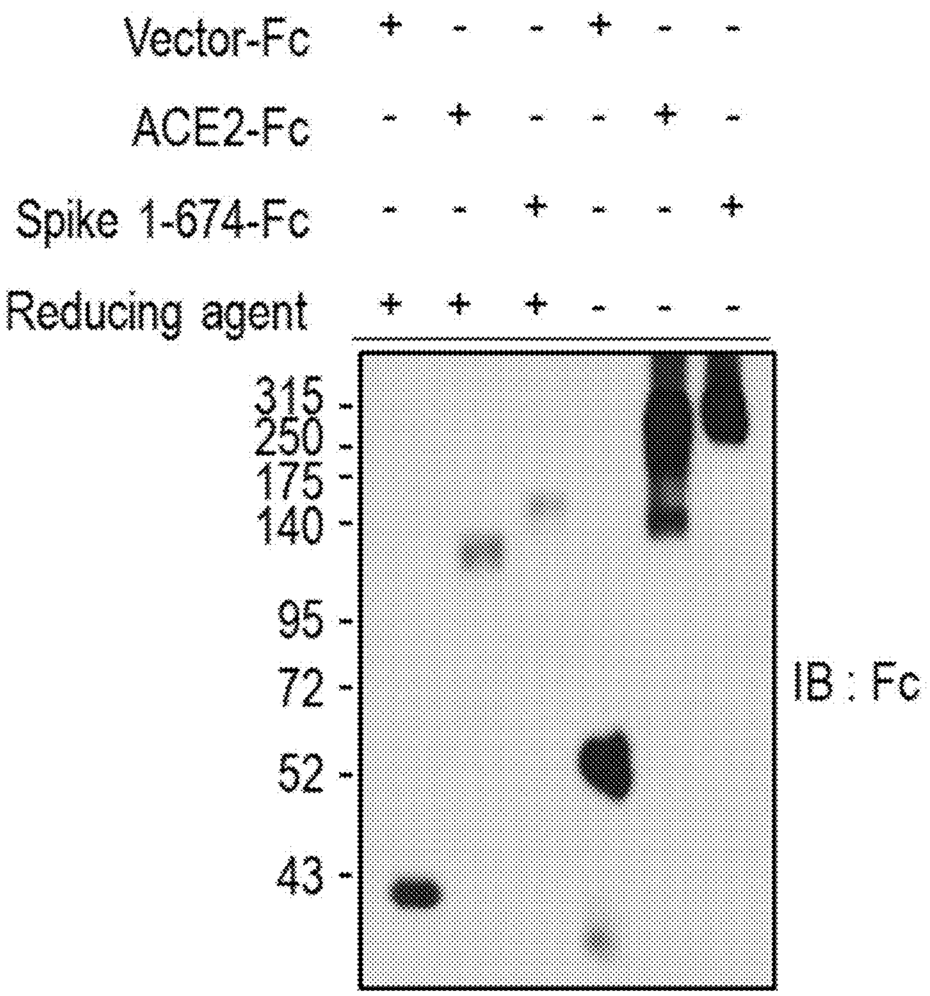
Figure 1F:
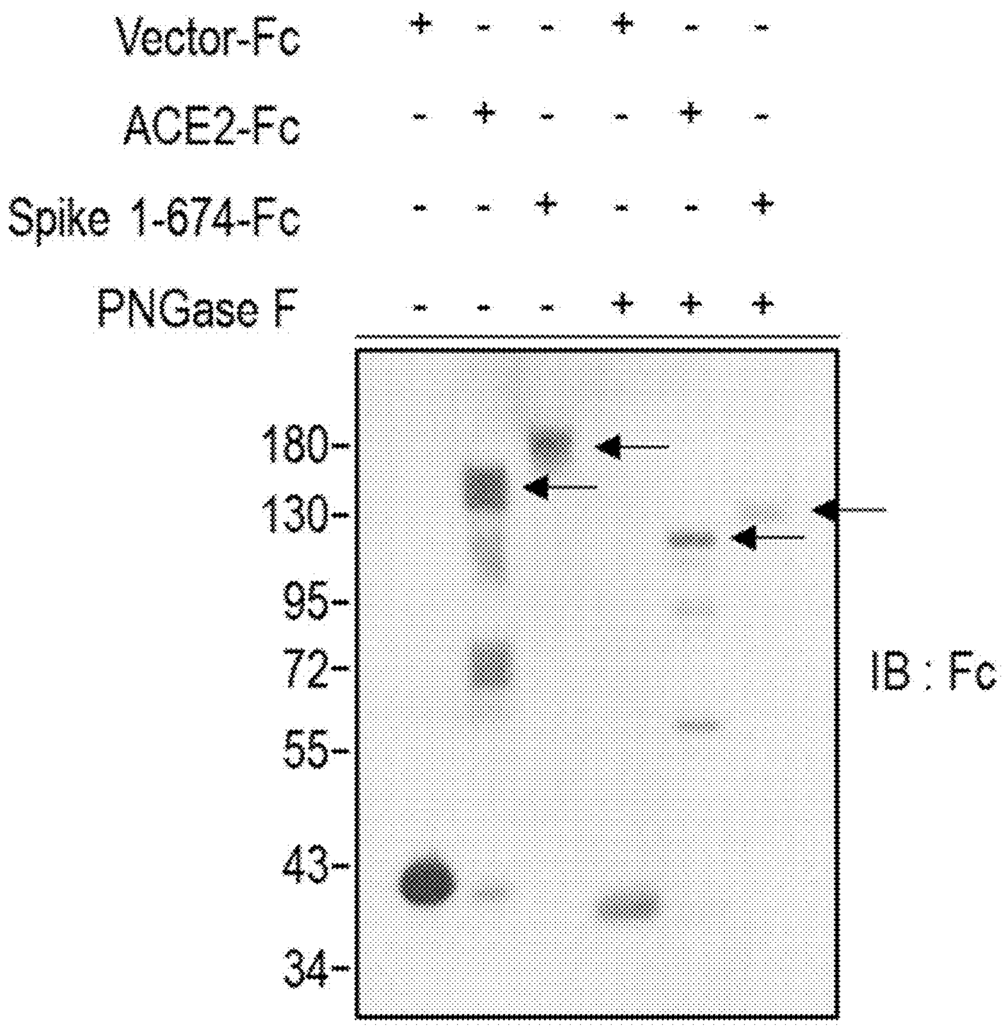

The ACE2-Fc fusion polypeptide in the cell culture supernatants were purified by Protein G Sepharose (Merck). A single band of ACE2-Fc was observed by Coomassie Brilliant Blue staining using reducing or nonreducing loading dye. FIG. 1C. The black arrows indicate the location of the induced target proteins was found to be specifically recognized by anti-ACE2 antibody (FIG. 1C). As shown in FIG. 1D, the ACE2-Fc fusion protein and can form a stable homodimer, which may enhance the neutralizing activity and the half-life of this decoy protein. Similar to ACE2-Fc fusion protein, Spike 1-674-Fc can also form stable homodimer. FIG. 1E. The ACE2-Fc and Spike 1-674-Fc protein were likely to be heavily N-glycosylated since size reduction was observed in SDS-PAGE after PNGase F treatment. FIG. 1F.

(ii) Assessment of Enzymatic Activity

Figure 2A:
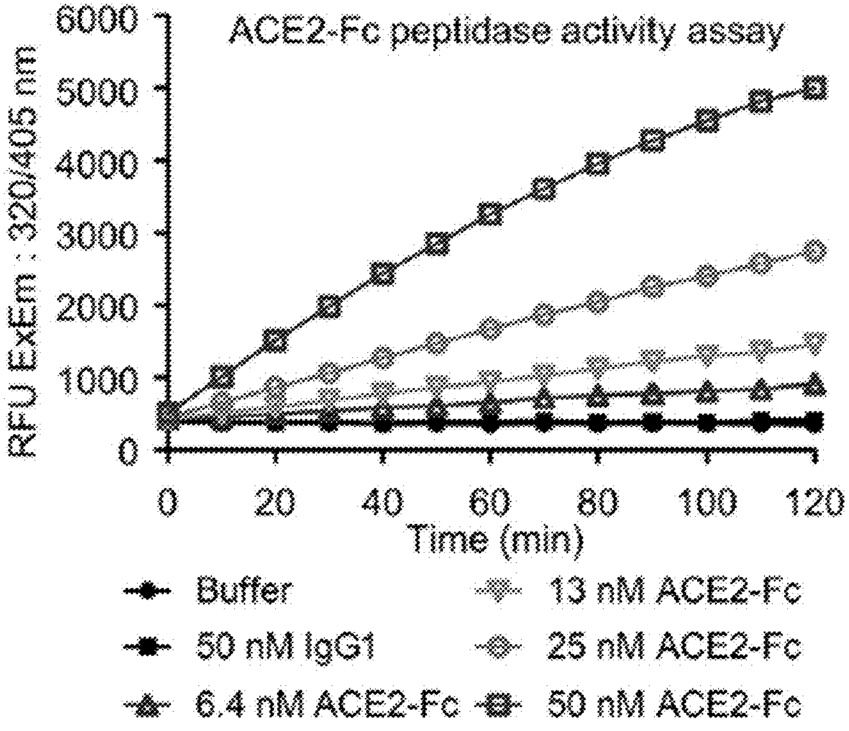
FIGS. 2A-2D include diagrams showing bioactivities of the ACE2-Fc fusion polypeptide.

Next, the enzyme activity of the purified ACE2-Fc fusion polypeptide was measured using fluorescent peptide substrate, Mca-Tyr-Val-Ala-Asp-Ala-Pro-Lys (Dnp)-OH (Mca: (7-Methoxycoumarin-4-yl) acetyl, Dnp: 2, 4-Dinitrophenyl) (ES007, R&D). In brief, ACE2-Fc was two-fold serially diluted starting at 50 nM in the reaction buffer (50 mM MES, 300 mM NaCl, 10 μM $ZnCl_2$, 0.01% Brij-35 pH 6.5). Five microliter of 1 mM peptide substrate was pre-mixed with 45 μL of reaction buffer, and co-incubated with variant concentration of ACE2-Fc. The fluorescence (Ex/Em=320/420 nm) was measured in a kinetic mode for 30 minutes to 2 hours at room temperature (25±3° C.) by a fluorescence reader. As shown in FIG. 2A, the purified ACE2-Fc fusion protein retained the peptidase activity as compared with human normal IgG and a blank control. The peptidase activity may enable ACE2-Fc to reduce angiotensin II mediated cytokine cascade during SARS-CoV-2 infection (Hirano & Murakami, 2020; *Immunity* 52(5):731-733).

Figure 2B:
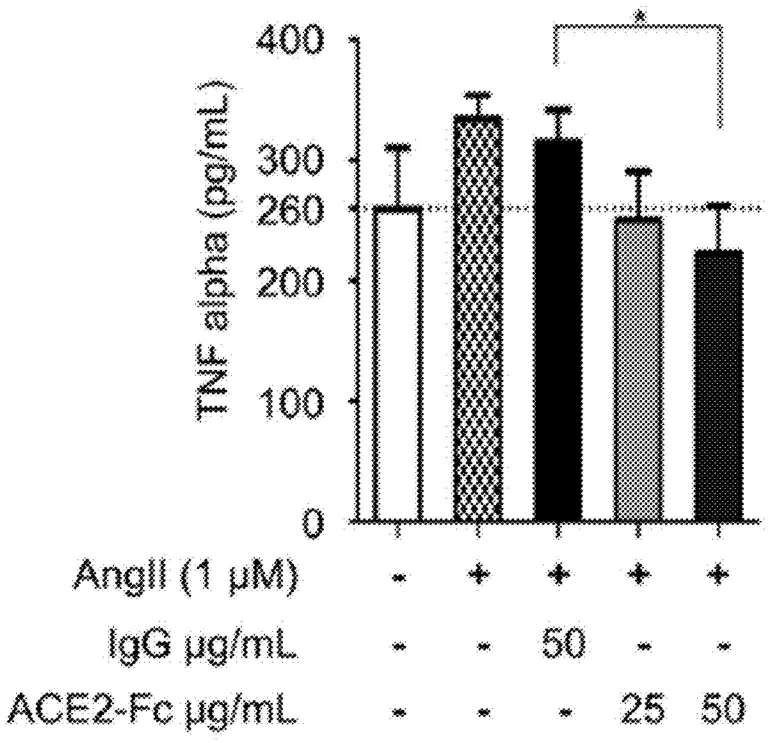
Figure 2D:
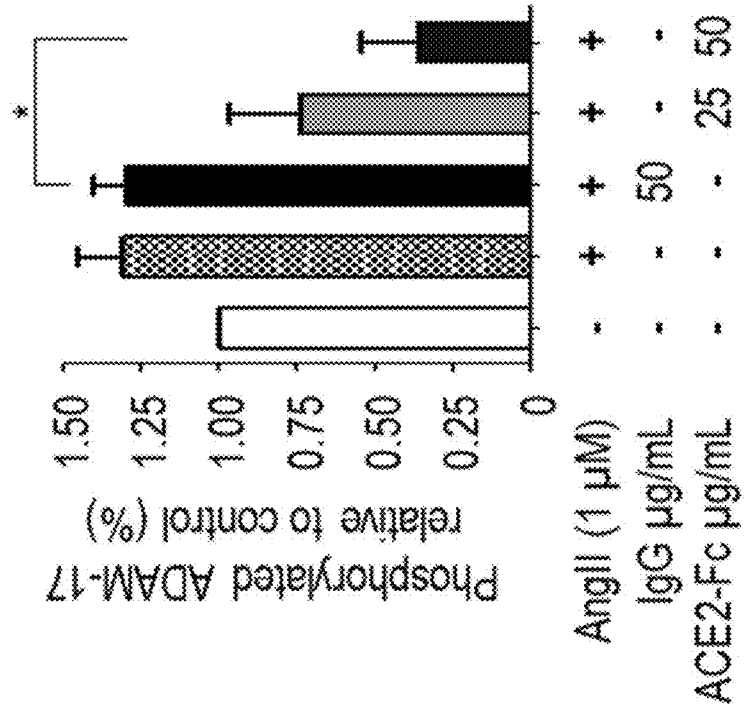
Figure 2C:
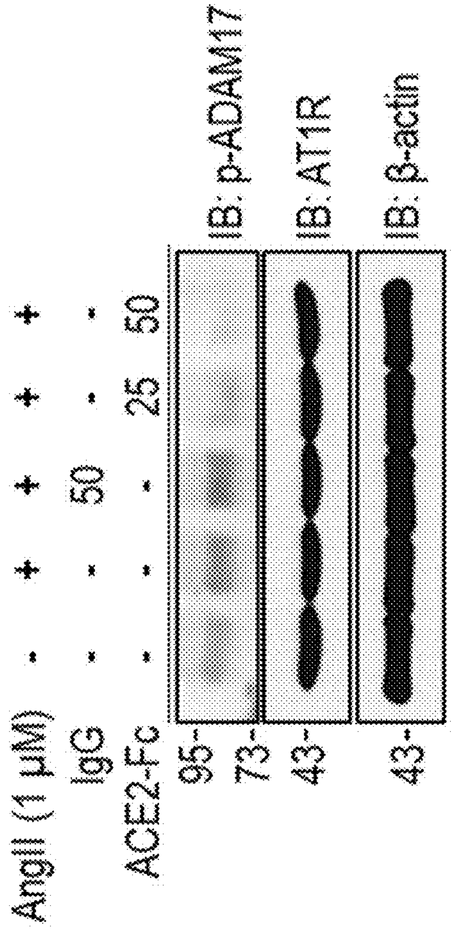

The effects of ACE2-Fc on Ang II-mediated inflammatory cascade were subsequently investigated, using TNF-α secretion as a readout. RAW264.7 macrophage cells ($1\times10^5$ cells/well) were seeded in a 12-well plate overnight. Angiotensin II (A9525, Sigma-Aldrich) was preincubated with or without ACE2-Fc at 37° C. for 30 min. Then, the mixtures were added to RAW264.7 cells for another 12 h. The TNF-α concentrations in the culture supernatants were measured using the ELISA kit (DY410, R&D Systems) according to the manufacturer's protocols. The absorbance at 450 nm in each well was determined using a VersaMax microplate reader (Molecular Devices). After the co-incubation of Ang II with ACE2-Fc, the ACE2-Fc significantly suppressed Ang II-induced TNF-α production (FIG. 2B) and phosphorylation of ADAM17 (a disintegrin and metalloprotease 17) (FIG. 2C).

(iii) Assessment of Binding to SARS-CoV-2 Spike Protein

An ELISA assay was performed subsequently to examine whether this purified ACE2-Fc fusion protein could bind to the SARS-CoV-2 Spike.

Briefly, fifty microliters of 50 ng/mL purified 1-674 or 319-591 Spike proteins were pre-coated on to the 96 well ELISA plate at 4° C. overnight. The plate was first washed three times with PBST (PBS containing 0.05% Tween-20) and blocked with blocking buffer (1% BSA, 0.05% $NaN_3$ and 5% sucrose in PBS) at room temperature for 30 minutes. After that, the plate was washed three times with PBST. Serially diluted ACE2-Fc-Biotin with or without soluble unlabeled ACE2-Fc or Spike 1-674 were pre-incubated at 37° C. for 1 hour. After that, the mixture was added to the 96 well plate and incubated at 37° C. for 1 hour. After that, the plate was washed three time with PBST and incubated with horseradish peroxidase (HRP)-conjugated streptavidin (1:500) at 37° C. for 30 minutes. After three-times wash with PBST, tetramethylbenzidine substrate (TMB) (T8665, Sigma) was added for 30 minutes before stopping the reaction by 50 μL of 1N $H_2SO_4$. HRP activity was measured at 450 nm using ELISA plate reader (VERSAMAX).

Figure 3A:
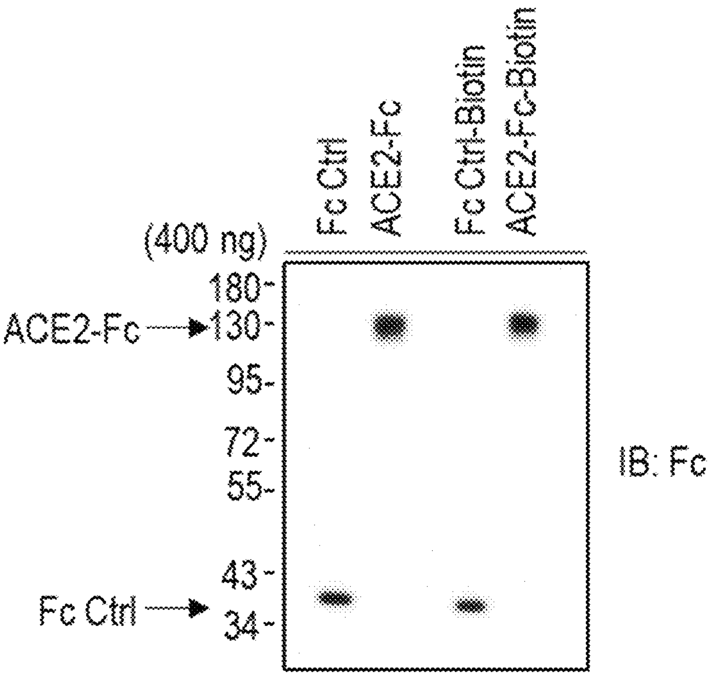
FIGS. 3A-3E include diagrams showing binding activity of ACE-Fc fusion polypeptide to Spike S1 subunit.
Figure 3B:
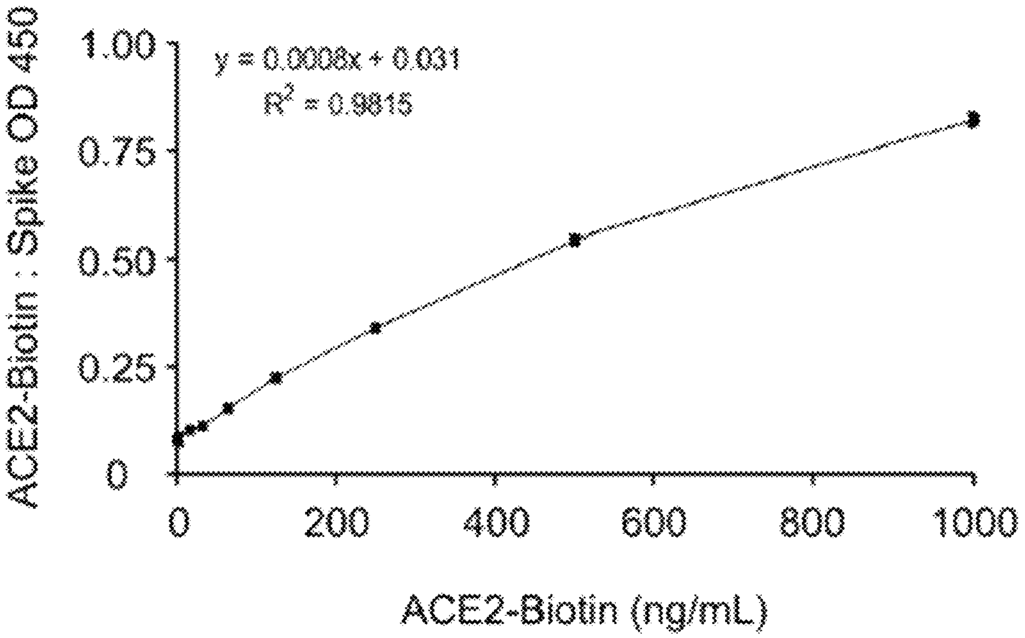
Figure 3C:
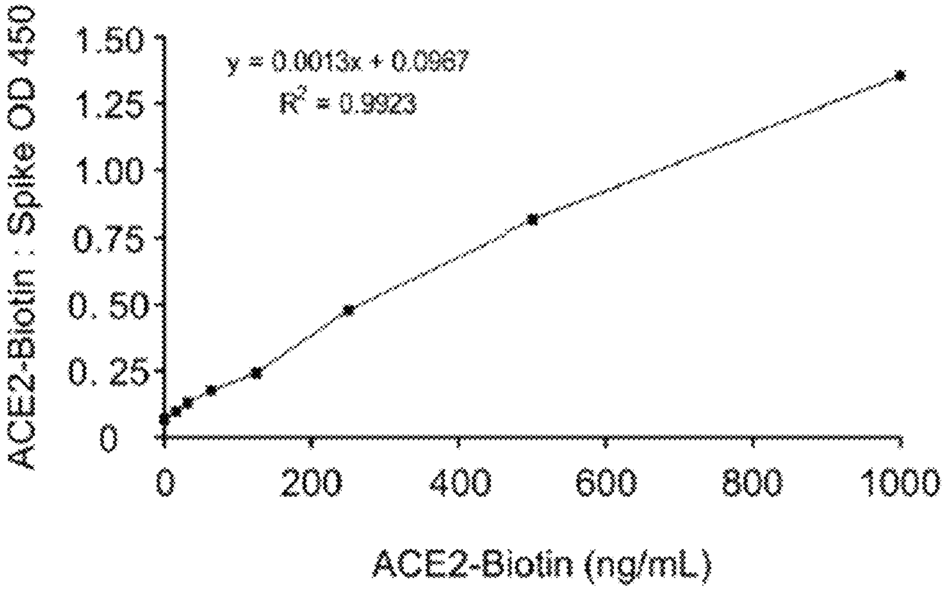
Figure 3D:
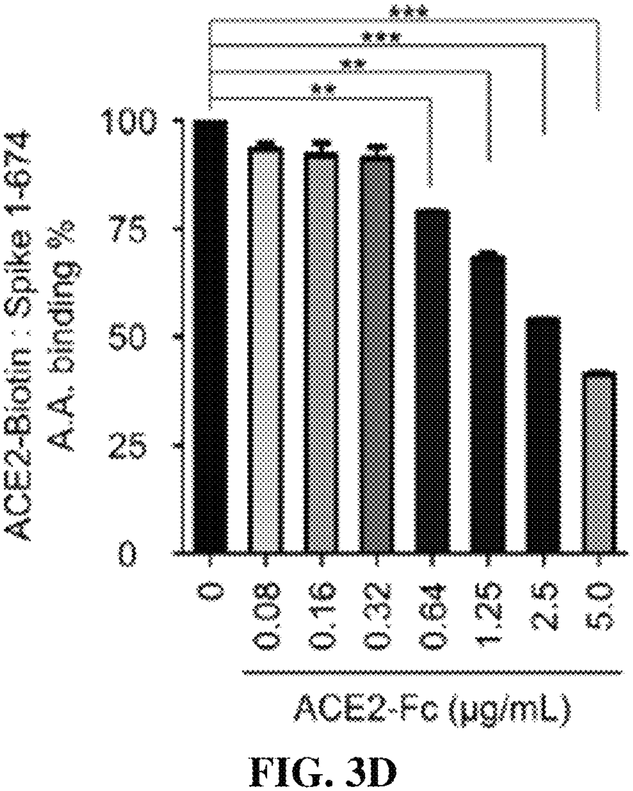
Figure 3E:
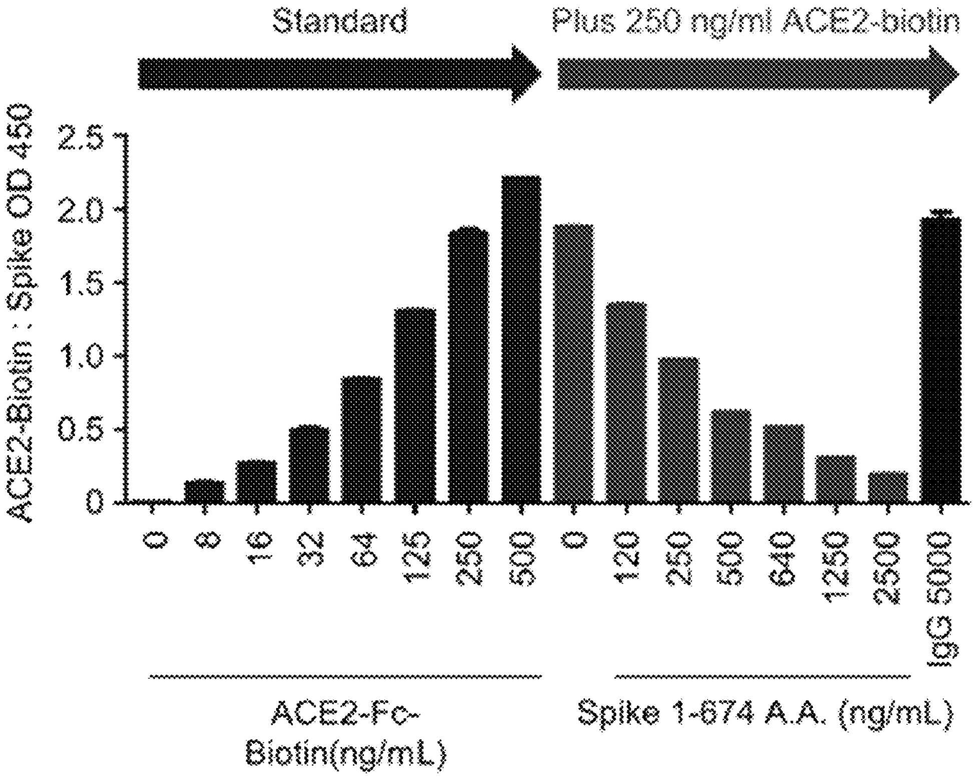

The ACE2-Fc was further modified with a monomer D-Biotin at its C-terminus by an Avi-tag affinity process (FIG. 3A). As shown in FIGS. 3B-3C, ACE2-Fc-Biotin, as the functional receptor, could interact with the 1-674 as well as the 319-591 truncated Spike proteins. The ACE2-Fc-Biotin/Spike S1 interaction was disrupted by 20-fold excess of unlabeled ACE2-Fc Decoy protein (FIG. 3D) or the Spike S1 subunit (FIG. 3E) in a dose-dependent manner.

Binding of the ACE2-Fc fusion polypeptide to Spike S1 subunit was further investigated via flow cytometry and immunofluorescence staining assays.

In a flow cytometry assay, ACE2-Fc was conjugated with green fluorescence using a FITC Labeling Kit (ab102884, Abcam). H1975-Spike-overexpressing cells ($2\times10^5$/reaction) were detached by 0.48 mM EDTA and then incubated with FITC-conjugated ACE2-FC or isotype control (Thermo Fisher Scientific) on ice for 1 h. After that, the cells were washed twice and re-suspended in cold PBS. The fluorescence levels were quantified by the FACSCanto flow cytometer (Becton Dickinson) and analyzed using the FlowJo software. The results show that ACE2-Fc bound to the cell surface of human lung adenocarcinoma H1975 cells expressing full-length Spike protein in a dose-dependent manner.

In an immunofluorescence staining assay, the H1975-Spike-expressing cells were fixed with 4% paraformaldehyde and blocked with 10% FBS. The cells were then stained with anti-Spike antibody (1:1,000) at 4° C. overnight and incubated with Alexa Fluor® 594 conjugated secondary antibody (1:500) at 37° C. for 1 h. Next, the cells were stained with FITC-conjugated ACE2-Fc at 4° C. overnight and mounted with ProLong™ Diamond Antifade Mountant with DAPI (Thermo Fisher Scientific). Images were taken with an LSM 700 laser scanning confocal microscope (Carl Zeiss). Co-localization of the FITC-conjugated ACE2-Fc and anti-Spike antibody was observed in this assay by confocal microscopy, further confirming the specific recognition of the Spike proteins by the ACE2-Fc.

Example 2. ACE2-Fc Inhibits SARS-CoV-2 Spike-Mediated Cell-Cell Fusion and Syncytia Formation Cell fusion and syncytia formation assays were performed as follows.

HEK293T cells were co-transfected with plasmid 5 μg of pCR3.1-Spike and 0.5 μg of pLKO AS2-GFP by lipofectamine 3000® (L3000015, Thermo Fisher Scientific) for 3 days before being used as effector cells (293T-S). H1975 lung adenocarcinoma cells and HEK293T cells were transduced with lentivirus encoding full-length ACE2 before being used as target cells (H1975-ACE2). H1975, H1975-ACE2, HEK293, and HEK293T ($7.5\times10^5$ cells/well) cells were seeded in the 24-well plate at 37° C. overnight. The 293T-S cells were detached with 0.48 mM EDTA for 5 min. The 293T-S ($1\times10^5$/reaction) cells were preincubated with normal human IgG or ACE2-Fc at 37° C. for 1 h. After that, the antibody and effector cell mixtures were added to target cells and incubated at 37° C. for 4 h or 24 h. Cells were fixed with 4% paraformaldehyde at room temperature for 30 min. The 293T/Spike/EGFP cells fused or unfused with HEK293T-ACE2 or H1975-ACE2 cells were counted under an inverted fluorescence microscope (Leica DMI 6000B fluorescence microscope). The percent inhibition of syncytia formation was calculated using the following formula: (100−(H−L)/(EL)×100). H represents the total green fluorescent score in the individual picture. L represents the green fluorescent score in the negative control group in which target cells were replaced by HEK293 or H1975). E represents the green fluorescent score in each picture in the IgG or ACE2-Fc groups. Each image of the green fluorescent score was determined by the MetaMorph's extensive analysis tools.

Figure 4A:
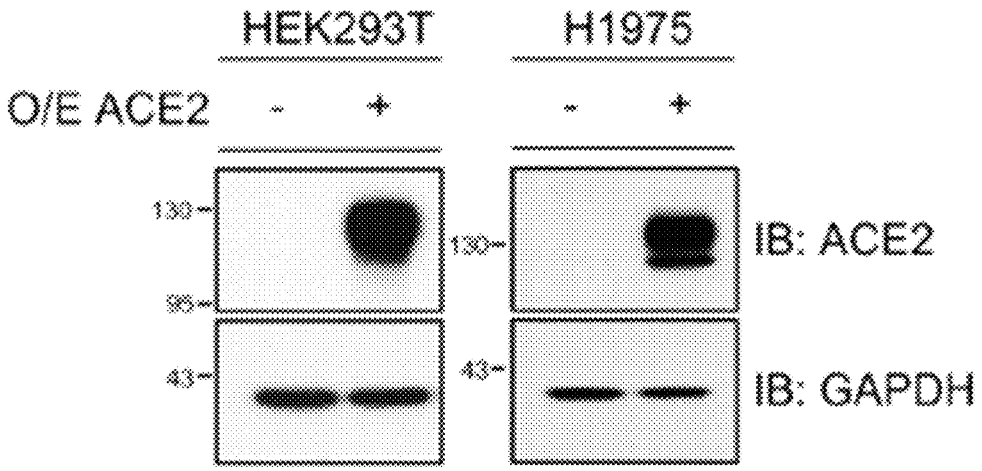
FIGS. 4A-4D include diagrams depicting the inhibitory activity of ACE2-Fc against Spike-induced cell-cell fusion and syncytia formation.

To determine whether the decoy fusion protein was able to inhibit SARS-CoV-2 fusion with the target cells, SARS-CoV-2 Spike protein and EGFP were transfected into the HEK293T cells as the effector cells (293T-S) and used the ACE2-stable-expressing HEK293T and H1975 cells as the target cells (293T-ACE2 and H1975-ACE2). Expression of ACE2 in both HEK293T cells and H1975 cells was shown in FIG. 4A. The target cells without ACE2 overexpression were used as controls. HEK293T cells were co-transfected with plasmid 5 μg of pCR3.1-Spike and 0.5 μg of pLKO AS2-GFP by lipofectamine 3000 (L3000015, Thermo Fisher Scientific) for 3 days before being used as effector cells (293T-S). H1975 lung adenocarcinoma cells and HEK293T cells were transduced with lentivirus encoding full-length ACE2 before being used as target cells (H1975-ACE2). H1975, H1975-ACE2, HEK293, and HEK293T ($7.5\times10^5$ cells/well) cells were seeded in the 24-well plate at 37° C. overnight. The 293T-S cells were detached with 0.48 mM EDTA for 5 min.

Figure 4B:
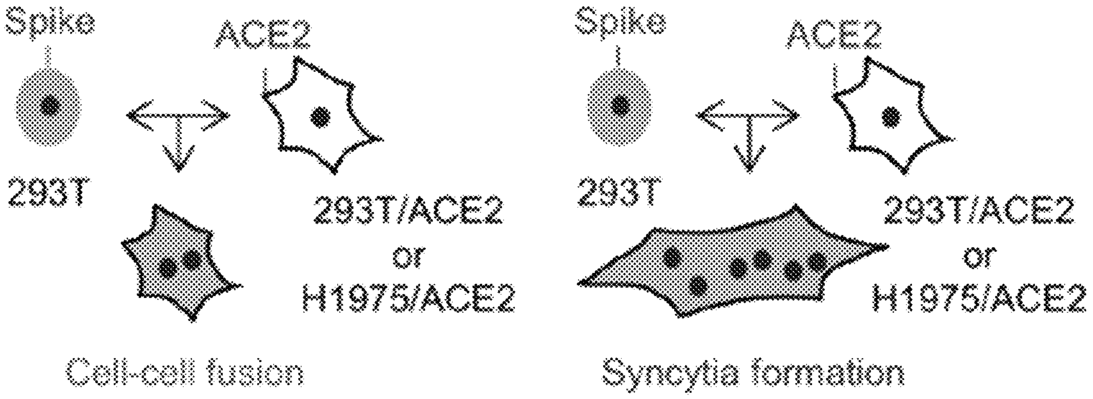
Figure 4D:
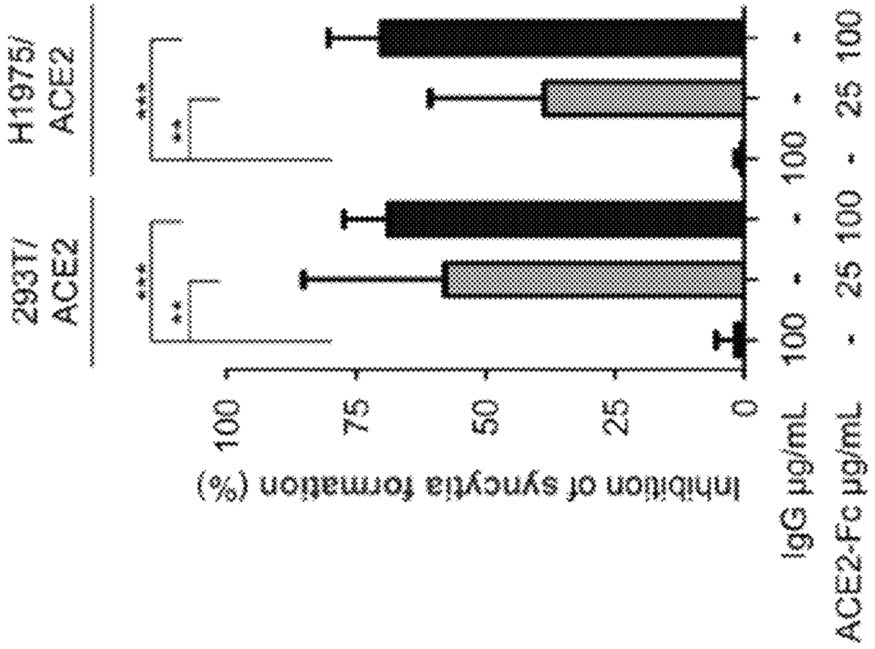
Figure 4C:
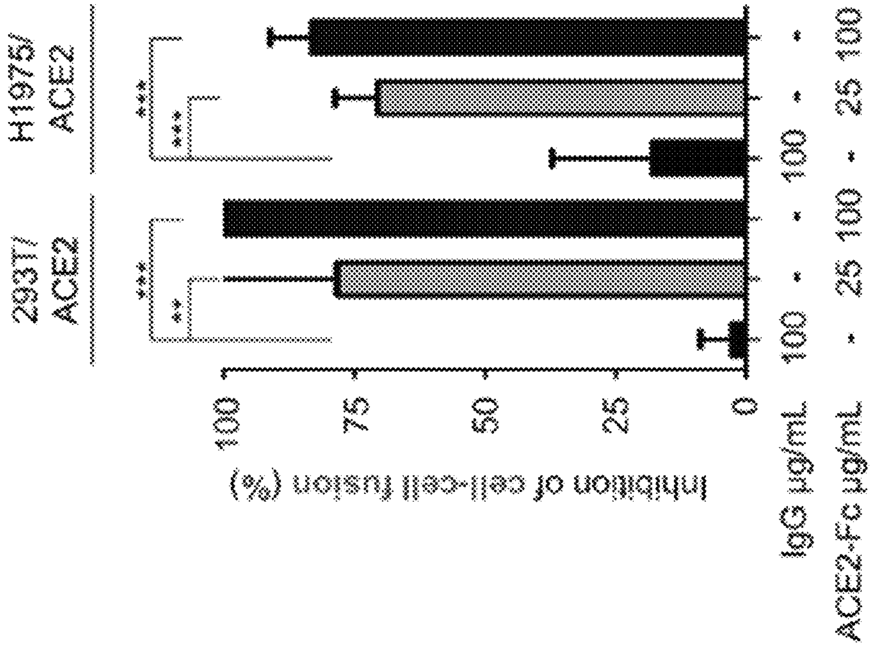

The effector cells (293T-S) were preincubated with ACE2-Fc or IgG at 37° C. for 1 h before mixing with the target cells or control cells and incubated at 37° C. for another 4 h (cell-cell fusion assay) or 24 h (syncytia formation assay, which is illustrated in FIG. 4B). Cells were fixed with 4% paraformaldehyde at room temperature for 30 min. The 293T/Spike/EGFP cells fused or unfused with HEK293T-ACE2 or H1975-ACE2 cells were counted under an inverted fluorescence microscope (Leica DMI 6000B fluorescence microscope). The percent inhibition of syncytia formation was calculated using the following formula: (100−(H−L)/(EL)×100). H represents the total green fluorescent score in the individual picture. L represents the green fluorescent score in the negative control group in which target cells were replaced by HEK293 or H1975). E represents the green fluorescent score in each picture in the IgG or ACE2-Fc groups. As shown in FIGS. 4C-4D, ACE2-Fc significantly impaired SARS-CoV-2 Spike-mediated cell-cell fusion and syncytia formation compared to the normal human IgG control in both the HEK293T and the H1975 cell systems. In addition, a dose-dependent inhibition of cell-cell fusion or syncytia was observed at increasing doses of ACE2-Fc in H1975 cell system. These results demonstrated that ACE2-Fc could block SARS-CoV-2 infection via abrogating virus-mediated cell-cell fusion and syncytium formation.

Example 3. Cytotoxicity and Stability Analysis of ACE2-Fc

The cell viability assay was determined according to the manufacturer's instructions (CellTiter 96® AQueous MTS, G1111, Promega). Briefly, $5\times10^3$ cells per well were seeded into 96-well plates in complete culture media. After 24 h, cells were treated with various concentrations of ACE2-Fc or IgG for another 72 h in complete culture media at 37° C. Twenty microliters of the MTS stock solution was added to each well of the treated cells. After another 1 h of incubation, absorption was measured at 490 nm by the spectrophotometer (Molecular Devices).

Plasma stability was assessed as follows. ACE2-Fc (2 μg/ml) was prepared in 50% normal human serum (Sigma, H4522) and incubated for 0, 1, 2, and up to 10 days at 37°

C. and then stored at −20° C. The ACE2-Fc binding activity was determined by the ELISA assay as described above.

Figure 5A:
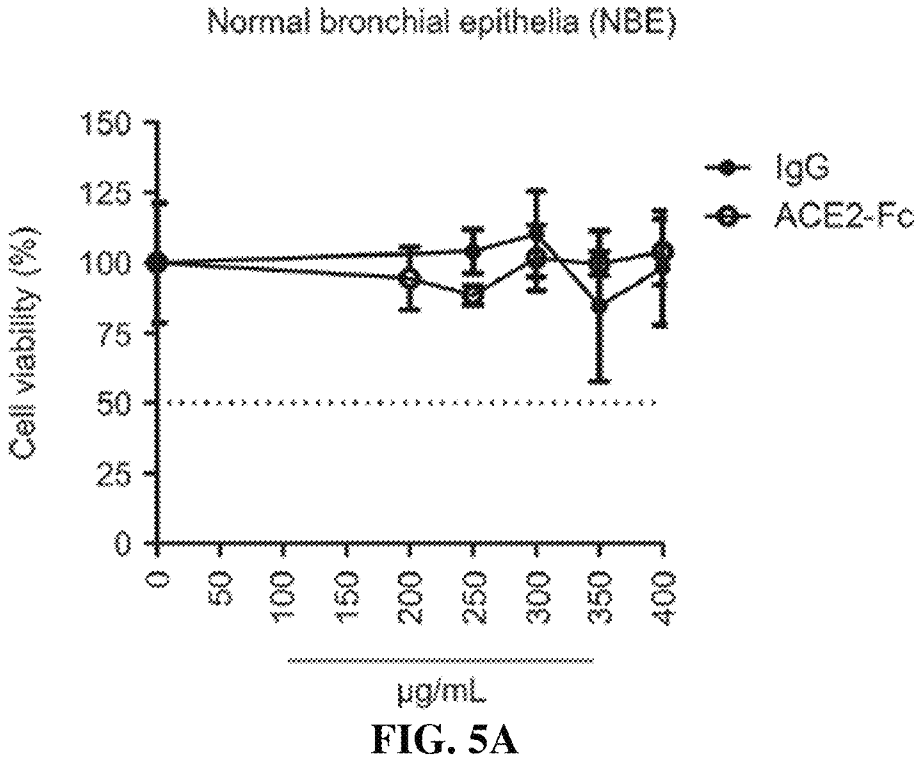
FIGS. 5A-5C include graphs depicting in vitro cytotoxicity and plasma stability of ACE2-Fc.
Figure 5B:
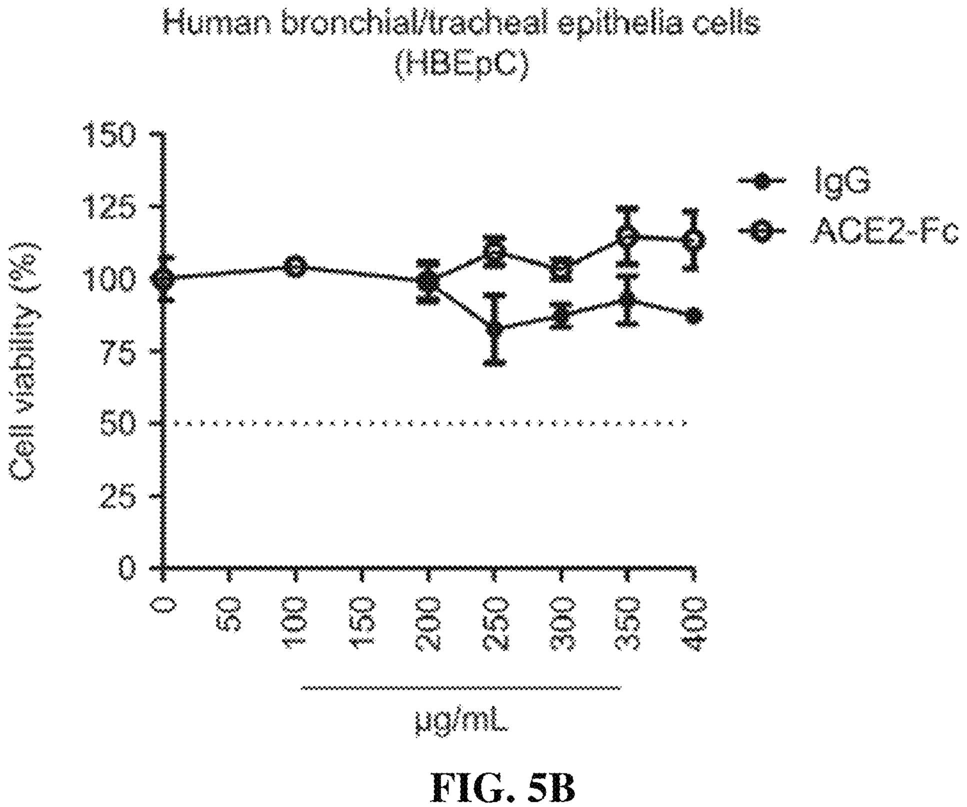
Figure 5C:
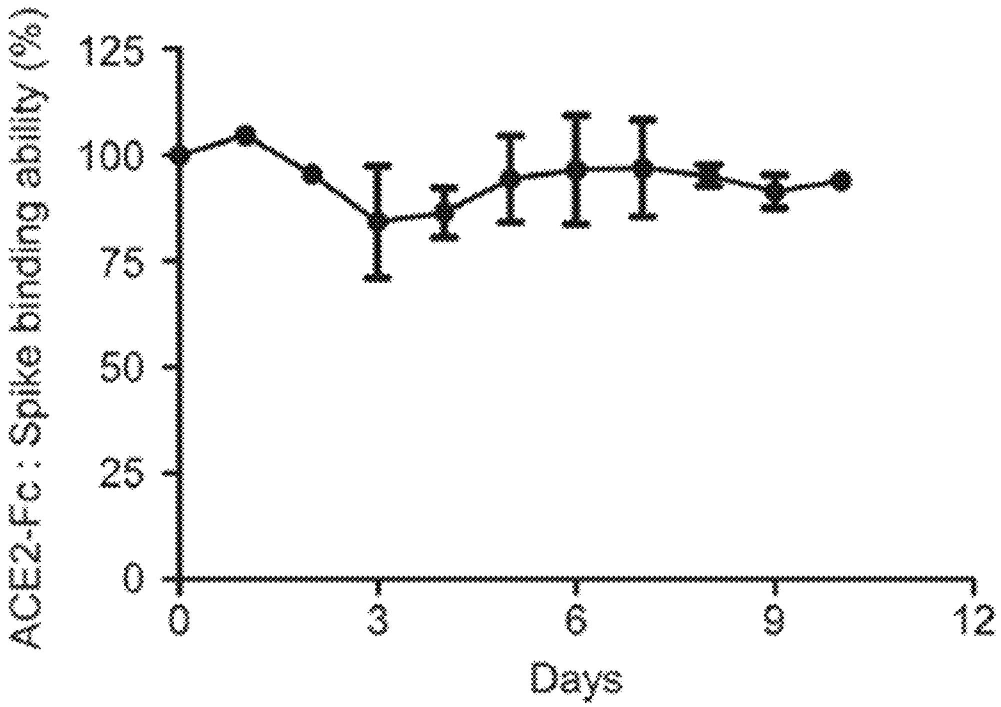

To examine the potential cytotoxicity of ACE2-Fc on normal cells, two different normal human bronchial epithelial (NBE) cells were treated with various concentrations of ACE2-Fc or IgG for 3 days before the cell viability assay. As shown in FIGS. 5A-5B, no cell toxicity was observed in these two normal cells at the concentration up to 400 μg/ml of ACE2-Fc. The stability of ACE2-Fc in serum was subsequently determined. Two μg/ml ACE2-Fc was incubated in 50% normal human serum at 37° C. for 0, 1, 2, and up to 10 days. The stability of ACE2-Fc was determined by assaying its binding ability to the Spike proteins in the ELISA assay. As shown in FIG. 5C, not a significant reduction of ACE2-Fc/Spike binding was observed up to 10 days. These results suggested that ACE2-Fc had no toxicity to epithelial cells and may be stable in serum for 10 days, which may facilitate its future clinical application.

Example 4. ACE2-Fc Blocks SARS-CoV-2 Entry and Replication

The SARS-CoV-2 Spike protein contains 22 N-linked oligosaccharides, which play a role for epitope masking and possibly immune evasion (Watanabe et al, 2020; *Science*. eabb9983). It is expected that up to 10 mutations on the RBD domain of the SARS-CoV-2 Spike protein may significantly enhance the affinity to human ACE2 (Junxian et al., 2020; bioRxiv 03.15.991844) could impede the development of therapeutic antibodies. Therefore, the strategy developed herein was to block virus infection using a decoy protein (ACE2-Fc).

(i) ACE2-Fc Fusion Polypeptide Blocks Entry of Pseudotyped Lentivirus into ACE2-Expressing Cells and Lung Organoids First, the Spike expressing pseudotyped lentivirus was generated by replacing the G protein of vesicular stomatitis virus to SARS-CoV-2 Spike protein, following a published method with minor modifications (Glowacka et al, 2011). In brief, HEK-293T cells were transiently transfected with pLAS2w.Fluc.Ppuro, pcDNA3.1-2019-nCoV-S and pCMV-ΔR8.91 by using TransITR-LT1 transfection reagent (Mirus). The culture medium was refreshed at 16 hours and harvested at 48 hours and 72 hours post-transfection. Cell debris was removed by centrifugation at 4,000×g for 10 minutes, and the supernatant was filtered through the 0.45-μm syringe filter (Pall Corporation). For pseudovirus purification and concentration, the supernatant was mixed with 0.2× volume of 50% PEG 8,000 (Sigma) and incubated at 4° C. for 2 hours. The pseudotyped lentivirus was then recovered by centrifugation at 5,000×g for 2 hours and resolved in sterilized phosphate-buffered saline, aliquoted, and then stored at −80° C.

The luciferase assay was used to estimate lentiviral titer. Briefly, the standard VSV-G pseudotyped lentivirus was generated by transient transfection of HEK293T cells with pLAS2w.Fluc. puro, pMDG, and pCMV-DR8.91 as described above. The transduction unit of VSV-G-pseudotyped lentivirus was estimated using the cell viability assay. The VSV-G pseudotyped lentivirus with a known transduction unit was used to estimate the lentiviral titer of the pseudotyped lentivirus with SARS-CoV-2 Spike protein. In brief, HEK293T cells stably expressing human ACE2 were plated onto 96-well plates 1 day before lentivirus transduction. For the titration of pseudotyped lentivirus, different amounts of lentivirus were added into the culture medium containing polybrene (final concentration of 8 μg/ml). Spin infection was carried out at 1,100 g in a 96-well plate for 15 min at 37° C. After incubating cells at 37° C. for 16 h, the culture medium containing virus and polybrene was removed and replaced with fresh DMEM containing 10% FBS. The expression level of luciferase was determined at 72 h postinfection by the Bright-Glo™ Luciferase Assay System (Promega). The relative light unit (RLU) of VSV-G pseudovirus-transduced cells was used as a standard to determine the virus titer.

Figure 6B:
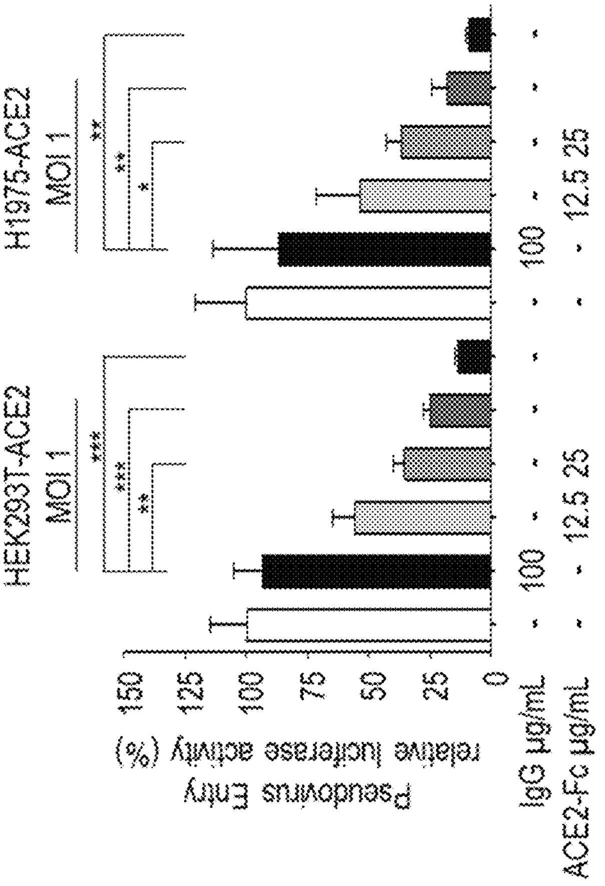
FIGS. 6A-6D include diagrams depicting blockage of Spike-expressing pseudovirus entry into ACE2-expressing cells by ACE2-Fc.
Figure 6A:
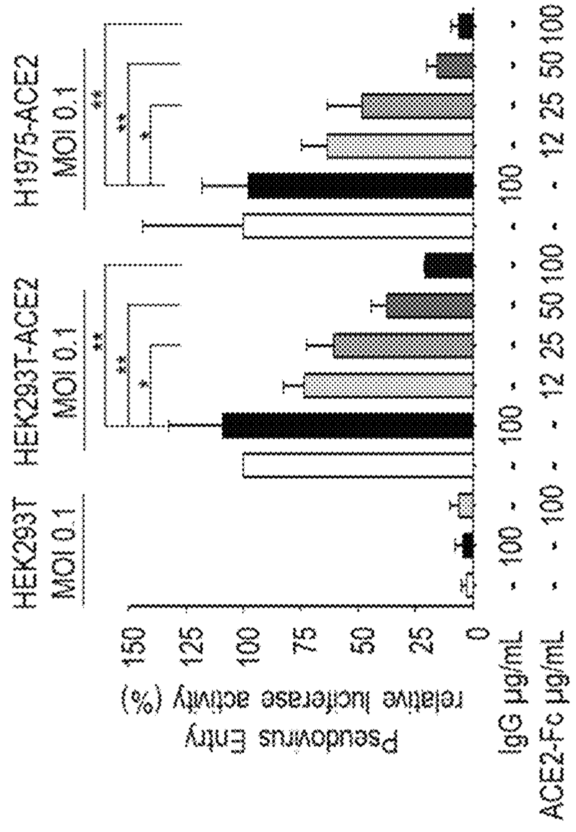

Pseudotyped virus was pre-incubated with either ACE2-Fc or human IgG1 for one hour at 37° C., before being added to the ACE2 overexpressing 293T cells for another one hour. After that, spin infection was performed at 1,100×g for 15 minutes at 37° C. before incubation at 37° C. for additional 4 hours. The cells were washed once with PBS, refreshed with culture medium, and incubated at 37° C. in a humidified atmosphere containing 5% $CO_2$ and 20% 02 for another 48 hr. Luciferase activity was measured according to the manufacturer's instructions (E1501, Promega). FIG. 6A shows that ACE2-Fc blocked pseudovirus entry into ACE2-expressing 293T. The dose-dependent blockage of viral entry by ACE2-Fc was not only observed in HEK293T cells, but also in another ACE2-expressing H1975 cell (H1975-ACE2) (FIG. 6A). A similar neutralization effect was observed in serum-free or 1% FBS culture medium (FIG. 6B).

Since the lung is the primary site for SARS-CoV-2 infection, an airway organoid model following the methods described herein was established to investigate the neutralization ability of ACE2-Fc against SARS-CoV-2 entry. In brief, human bronchial/tracheal epithelial cells (502-05a, Cell APPLICATIONS) were suspended in 10 mg/ml cold Corning Matrigel Growth Factor Reduced (GFR) Basement Membrane Matrix (356230, CORNING), and 50 μl drops of the cell suspension were solidified on prewarmed 24-well culture plates at 37° C. with 5% $CO_2$ for 10-20 min. Five hundred microliters of airway organoid medium was added to each well, and the medium was changed every 2-3 days. Airway organoids were passaged every 2 weeks. For passaging, airway organoids were first mechanically sheared through a flamed glass Pasteur pipette and further dissociated by incubation with TrypLE select enzyme (12563011, Thermo Fisher Scientific). The dissociated organoid fragments were collected by centrifugation at 400 g for 5 min and reseeded as above at the ratios of 1:2 to 1:4.

Airway organoids were first washed with PBS and fixed with 4% paraformaldehyde for 20 min at room temperature. Next, the fixed airway organoids were processed and embedded in paraffin. Then, the blocks were cut into 3-μm thick sections. For hematoxylin and eosin (H&E) staining, the sections were deparaffinized, rehydrated, stained with H&E, and examined using an Olympus BX51 Microscope with a DP73 Olympus Color camera. For immunofluorescence staining, the sections were deparaffinized, rehydrated, and subjected to antigen retrieval by treatment with 0.1% trypsin in PBS at 37° C. for 30 min. Then, the sections were blocked with 5% bovine serum albumin in PBS at room temperature for 30 min. The sections were incubated with primary antibodies overnight at 4° C. (anti-p63, ab124762, Abcam, 1:50; anti-SCGB1A1, sc-365992, Santa Cruz, 1:50; anti-acetylated a-tubulin, sc-23950, Santa Cruz, 1:50; anti-mucin 5AC, MS-145, Thermo Fisher Scientific, 1:50; anti-ACE2, ab108209, Abcam, 1:100; anti-TMPRSS2, sc-515727, Santa Cruz, 1:50), washed three times with PBS, incubated with secondary antibodies (Alexa Fluor 488® goat anti-rabbit, A11034, Thermo Fisher Scientific, 1:500; Alexa Fluor 488° goat anti-mouse, A11001, Thermo Fisher Scientific, 1:500)

for 1 h at room temperature, washed three times with PBS, incubated with fluorophore-conjugated Phalloidin (Phalloidin-TRITC, P1951, Sigma-Aldrich, 1:200), washed three times with PBS, and mounted with prolonged Diamond antifade mountant with DAPI (P36962, Thermo Fisher Scientific). The sections were imaged on a Zeiss LSM 510 Meta Inverted confocal microscope and processed using Zeiss LSM Image Browser software.

The derived airway differentiation organoids were successfully established and composed of several airway epithelial cells with specific markers, including basal (P63), secretory (club cell marker secretoglobin family 1A member 1 (SCGB1A1) and secretory cell marker mucin 5AC (MUC5AC)), and multiciliated cells (cilia marker acetylated a-tubulin). Of note, unlike the A549 or the parental human normal bronchial epithelial cells (HBEpc), these airway organoids expressed a high-level of ACE2 in addition to TMPRSS2 (FIG. 6C).

The neutralization ability of ACE2-Fc for Spike-expressing pseudotyped virus was then examined in the airway organoid model. ACE2-Fc was serially diluted twofold in culture medium starting at 100 μg/ml or 200 μg/ml. ACE2-Fc and pseudovirus were pre-incubated at 37° C. for 1 h. After that, the ACE2-Fc fusion polypeptide and virus mixtures were added to ACE2-expressing HEK293T cells, and spin infection was performed at 1,100 g for 15 min at 37° C. before incubation at 37° C. for an additional 4 h. The cells were washed once with PBS, refreshed with culture medium, and incubated at 37° C. in a humidified atmosphere containing 5% $CO_2$ and 20% $O_2$ for another 48 h. Luciferase activity was determined according to the manufacturer's instructions (E1501, Promega).

Different concentrations of ACE2-Fc were mixed with $1.0\times10^5$ PFU of pseudotype SARS-CoV-2 for 60 min at 37° C. in a final volume of 500 μl of airway organoid medium. The ACE2-Fc and virus mixtures were added to the Airway organoids following the procedures described in the Section on pseudotype SARS-CoV-2 infection. At 72 h, organoids were harvested, and the luciferase activities were measured according to the manufacturer's instructions (E1501, Promega).

Figure 6D:
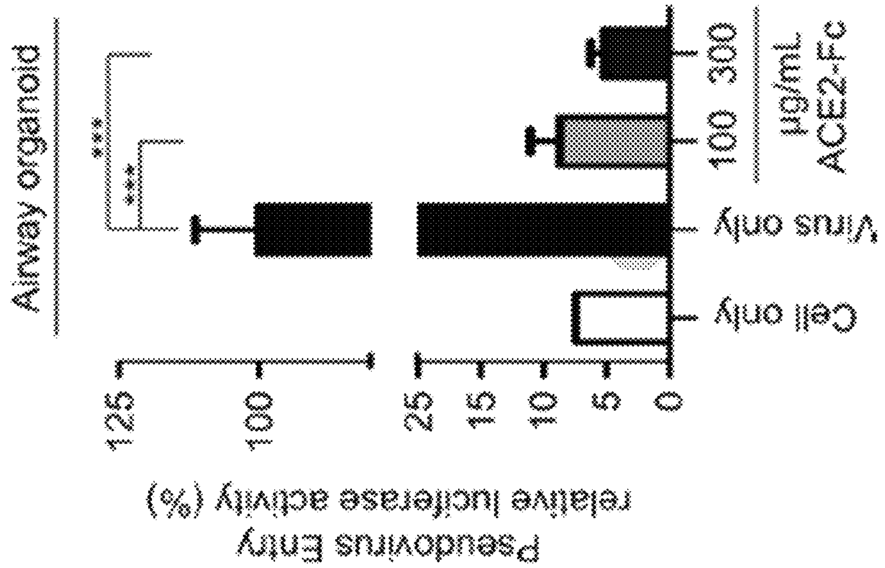
Figure 6C:
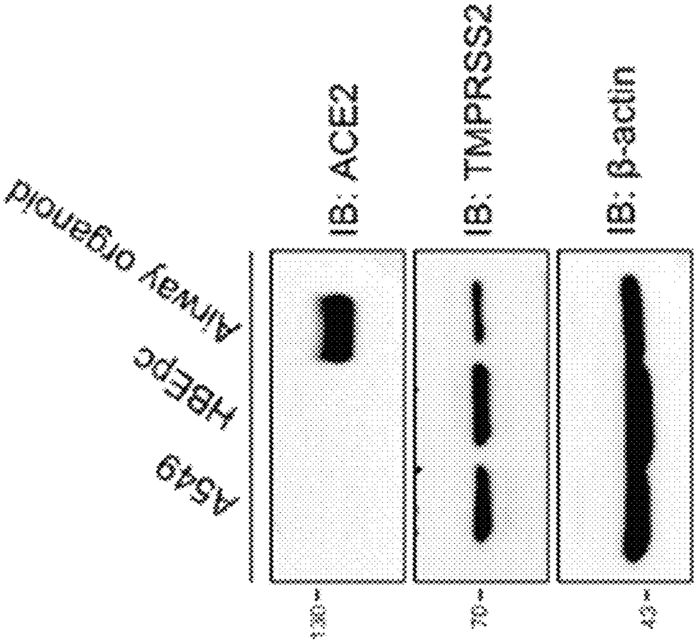

As shown in FIG. 6D, the airway organoids were susceptible to virus entry and the ACE2-Fc significantly blocked virus entry at the concentration of 100 μg/ml. These findings indicated that ACE2-Fc can inhibit entry of SARS-CoV-2 Spike-expressing pseudotyped virus entry into ACE2-expressing cells, including the airway organoids.

(ii) ACE2-Fc Fusion Polypeptide Blocks SARS-CoV-2 Entry and Replication

The viral entry blocking effect of ACE2-Fc was further confirmed using real SARS-CoV-2 isolated from patients suffering from COVID-19 infection.

Sputum or throat swab specimens obtained from SARS-CoV-2-infected patients were maintained in the viral-transport medium. The specimens were propagated in VeroE6 cells in DMEM supplemented with 2 μg/ml tosylsulfonyl phenylalantyl chloromethyl ketone (TPCK)-trypsin (Sigma-Aldrich). Culture supernatants were harvested when more than 70% of cells showed cytopathic effects. The full-length genomic sequences of the derived clinical isolates were determined and submitted, along with the patients' travel history and basic information, to the GISAID database. The virus strains used in this study include SARS-CoV-2/NTU03/TWN/human/2020 (Accession ID EPI_ISL_413592), SARS-CoV-2/NTU13/TWN/human/2020 (Accession ID EPI_ISL_422415), SARS-CoV-2/NTU14/TWN/human/2020 (Accession ID EPI_ISL_422416), SARS-CoV-2/NTU18/TWN/human/2020 (Accession ID EPI_ISL_447615), SARS-CoV-2/NTU25/TWN/human/2020 (Accession ID EPI_ISL_447619) and SARS-CoV-2/NTU27/TWN/human/2020 (Accession ID EPI_ISL_447621). The virus titers were determined by plaque assay described below.

Figure 7A:
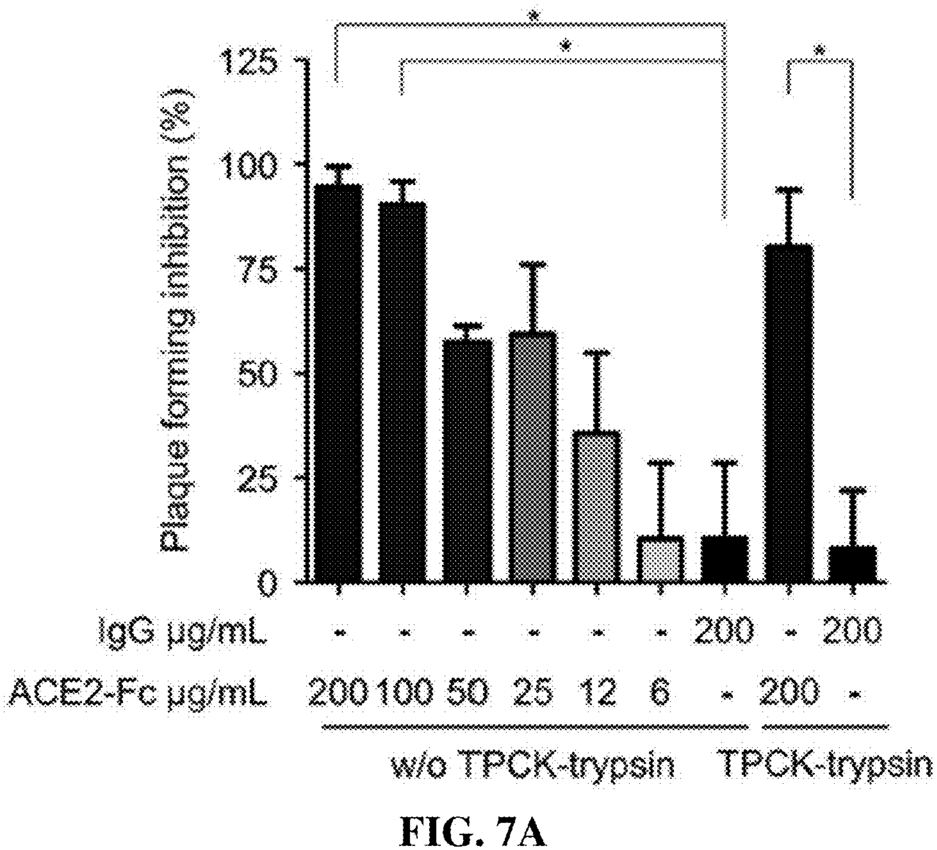
FIGS. 7A-7F include diagrams depicting blockage of SARS-CoV-2 entry into host cells by ACE2-Fc.

Vero E6 cells were seeded to the 24-well culture plate in DMEM with 10% FBS and antibiotics one day before infection. SARS-CoV-2 isolated from patients (4000 plaque forming unit, PFU) was incubated with ACE2-Fc proteins for 1 hour at 37° C. before adding to the Vero E6 cell monolayer for another one hour. Subsequently, virus-ACE2-Fc mixtures were removed and the cell monolayer was washed once with PBS before covering with media containing 1% 5-methylcellulose and further cultured for another for 5-7 days. The cells were fixed with 10% formaldehyde overnight. After removal of overlay media, the cells were stained with 0.7% crystal violet and the plaques were counted. The percentage of inhibition was calculated as $[1-(VD/VC)]\times100\%$, where VD and VC refer to the virus titer in the presence and absence of the compound, respectively. Pre-incubation of the SARS-CoV-2 isolated from patients with ACE2-Fc blocked the plaque formation in the Vero E6 cells (FIG. 7A). The EC50 value of neutralization effect of ACE2-Fc was 23.8±5.94 μg/mL.

Figure 7B:
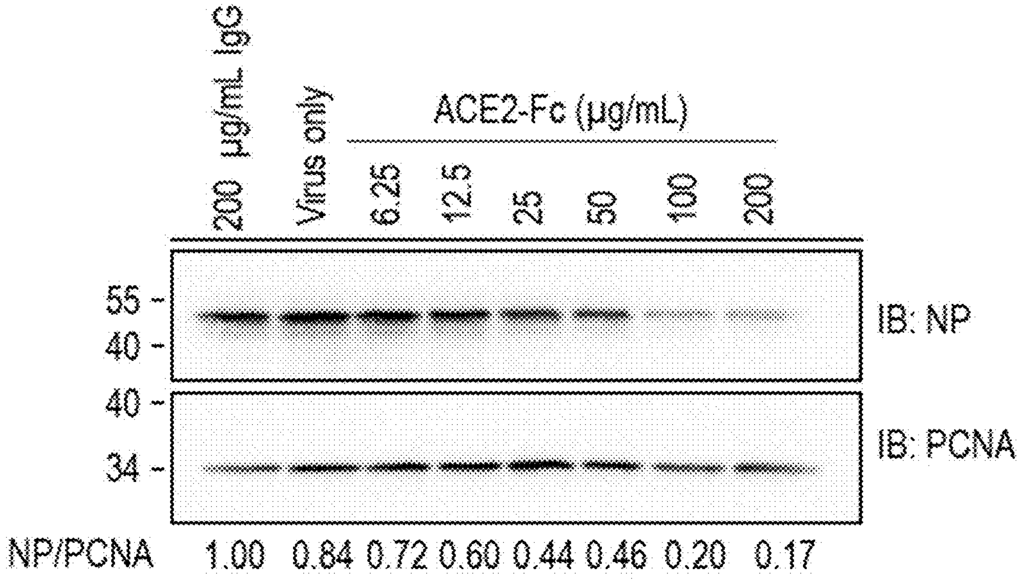

The inhibitory effect was subsequently verified by yield reduction assay. In brief, Vero E6 cells were seeded to the 24-well culture plate in DMEM with 10% FBS and antibiotics one day before infection. SARS-CoV-2 (multiplicity of infection, MOI=1) was incubated with ACE2-Fc proteins for 1 hour at 37° C. before adding to the cell monolayer for another one hour. After removal of virus inoculum, the cells were washed once with PBS and overlaid with 0.5 mL medium for 24 hours at 37° C. The next day, the culture supernatants were harvested for RNA extraction, and the cells were retrieved for protein, RNA extraction, and immunofluorescence assay, individually. The amount of viruses in the supernatants and infected cells was determined by qPCR using the protocol provided by the WHO (virologie-ccm.charite.de). Quantitative PCR of E gene was performed using the iTaq™ Universal Probes One-Step RT-PCR Kit (172-5140, Bio-Rad, USA) and the Applied Biosystems 7500 Real-Time PCR software (version 7500SDS v1.5.1). Plasmid containing partial E fragment was used as the standards to calculate the amount of viral load in the specimens. The percentage inhibition of virus yield was calculated as $[1-(Vd/Vc)]\times100\%$, where Vd and Vc refer to the virus copies in the presence and absence of the test compound, respectively. As shown in FIG. 7B, pretreatment of SARS-CoV-2 with ACE2-Fc decreased SARS-CoV-2 nucleoprotein expression.

Figure 7C:
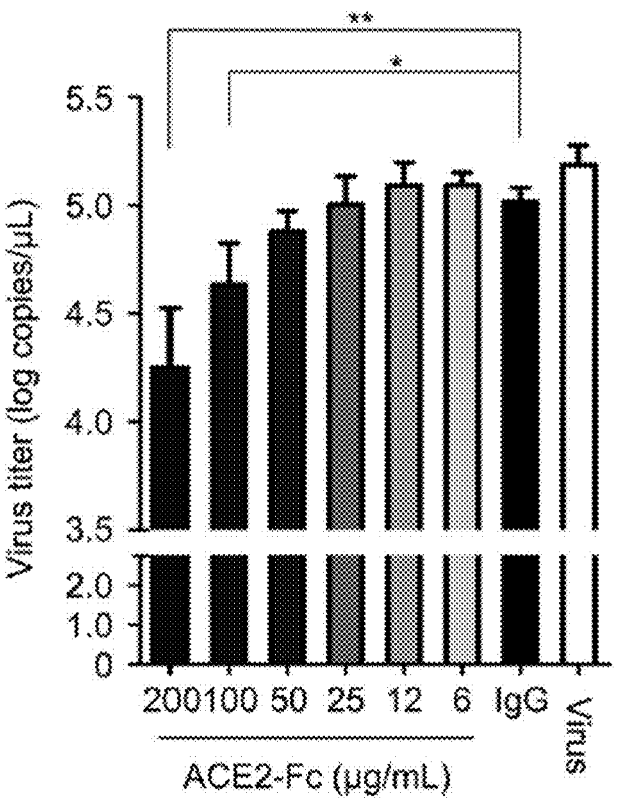
Figure 7D:
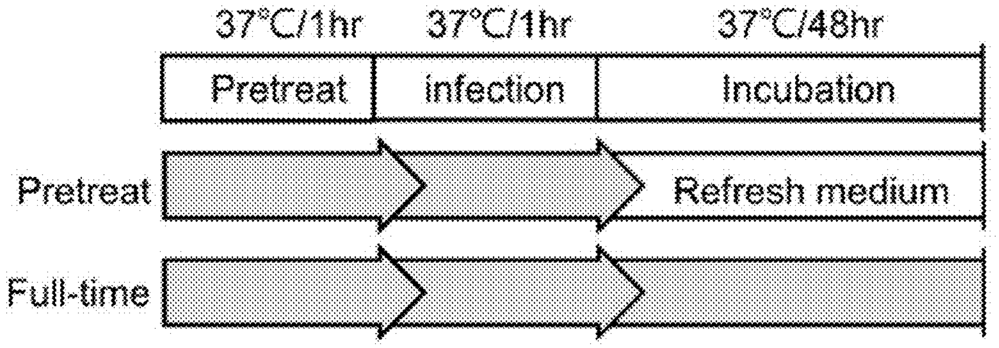
Figure 7F:
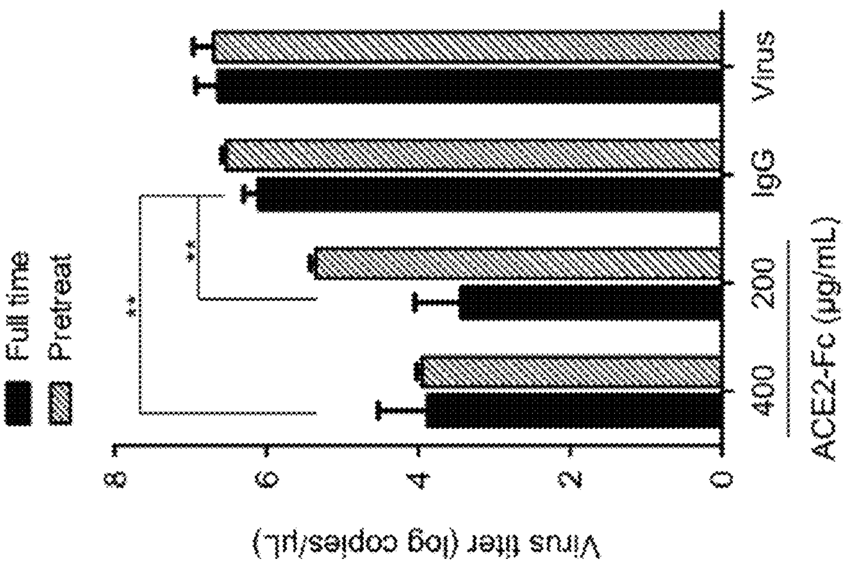
Figure 7E:
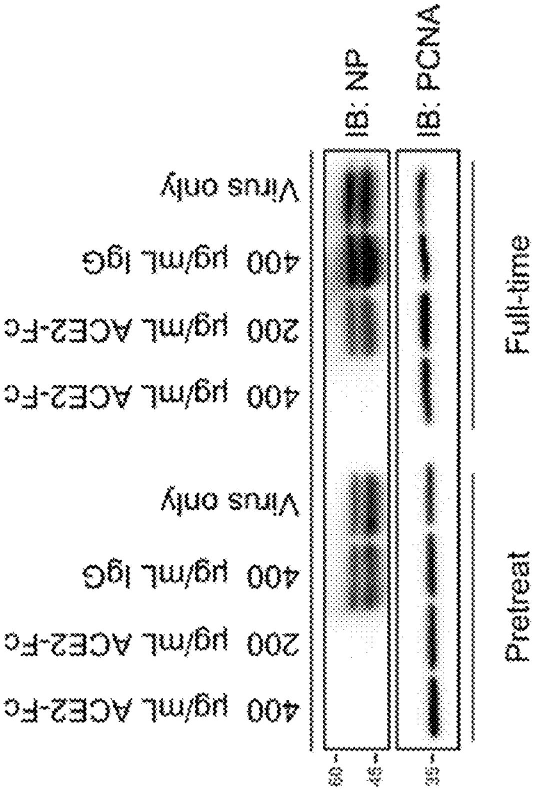

Pretreatment of SARS-CoV-2 with ACE2-Fc also reduced the SARS-CoV-2 RNA copies in the culture supernatant (FIG. 7C). In addition, the incubation period of virus-ACE2-FC was extended from 1 to 48 hours to examine whether resistant viruses would emerge (FIG. 7D). Comparable inhibitory effects on viral protein expression and supernatant viral RNA were observed when ACE2-Fc was present in the culture medium for 48 hours, as compared to the pretreatment group (FIGS. 7E-7F).

Figure 8A:
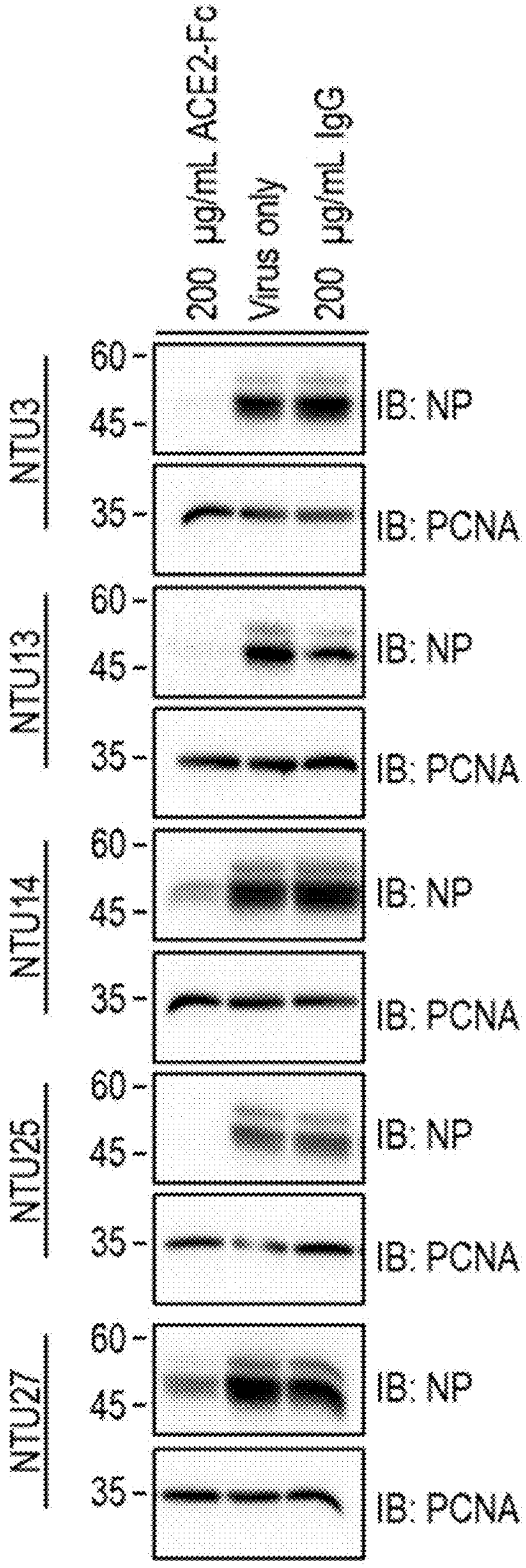
FIGS. 8A-8C include diagrams depicting neutralization activity of ACE2-Fc on different SARS-CoV-2 strains.
Figure 8B:
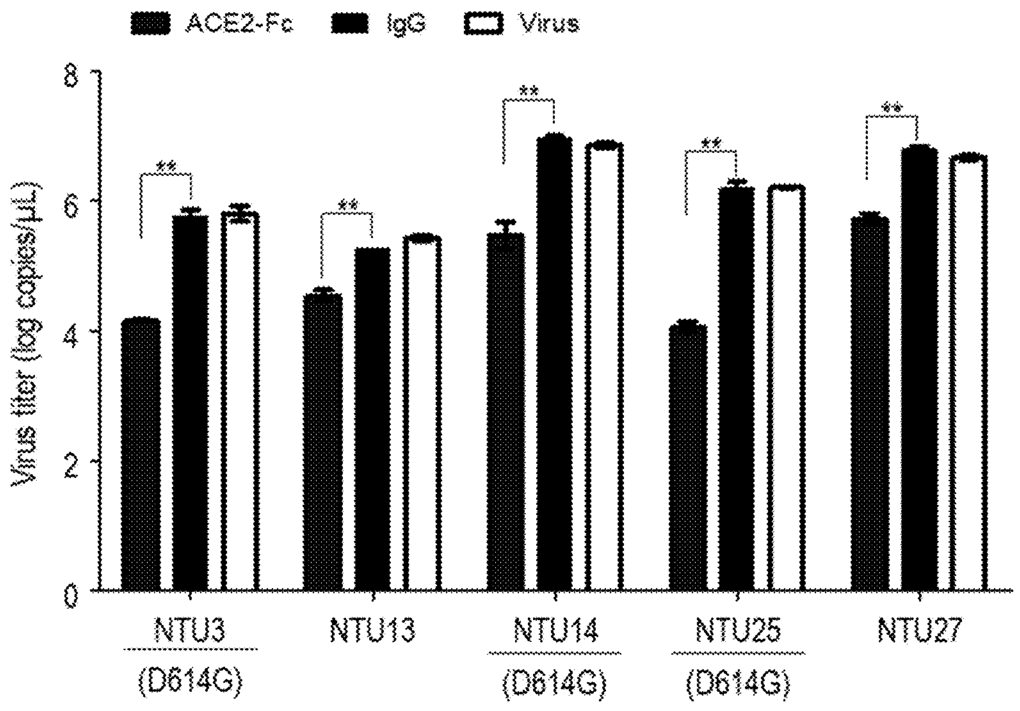
Figure 8C:
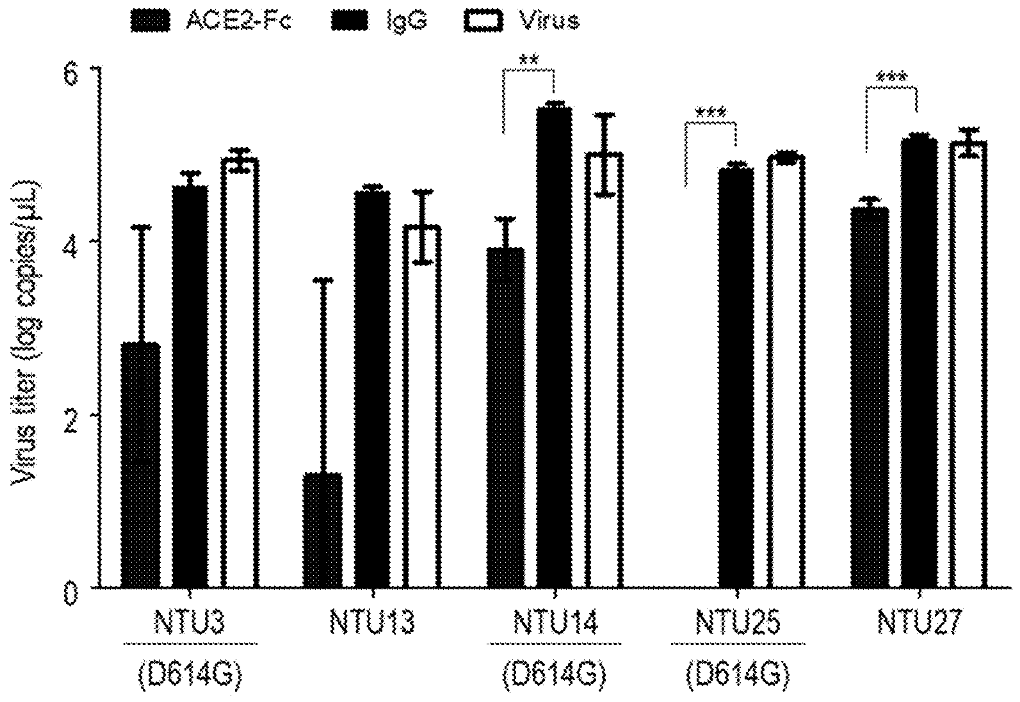

To determine whether ACE2-Fc also exhibited inhibitory effects on other circulating SARS-CoV-2 strains, five other clinical SARS-CoV-2 strains, NTU3, NTU13, NTU14, NTU25, and NTU27, were included for analysis. NTU3, NTU14, and NTU25 strains harbor the D614G mutation, which has been known to increase the viral infectivity. As shown in FIGS. 8A-8C, ACE2-Fc exhibited a potent ability to block SARS-CoV-2 protein expression (FIG. 8A) and viral RNA in the supernatants and infected cells (FIGS. 8B-8C).

Example 5. ACE2-Fc Induced Degranulation of Natural Killer (NK) Cells

Proteins fused to the Fc domain enable these molecules to interact with Fc receptors, which are critical for the induction of immune responses (Czajkowsky et al., 2012). Among these, antibody-dependent cellular cytotoxicity (ADCC) is an adaptive immune response, mainly mediated by the natural killer (NK) cells. After the specific interactions between antibodies or Fc fusion proteins with specific antigens on the cell surface of infected cells, cross-linking of the Fc domain activates the CD16 (FccRIII) receptor to trigger degranulation (CD107a on the cell membrane) and cytokine production (IFN-c and TNF-a) of NK cells. Recently, the RBD-specific antibodies from an individual infected with SARS-CoV in 2003 induced nearly 10% ADCC against SARS-CoV-2. Therefore, experiments were conducted to examine whether ACE2-Fc could induce primary human NK cell activation.

Human primary NK cells were thawed from cryogenic tubes and cultured in the NK MACS medium (Miltenyi Biotec) as described by the manufacturer's protocol. Forty-eight hours before the assay, NK cells were activated by 1,000 U/ml recombinant human IL-2 (Peprotech). To initiate cytotoxicity, 50,000 NK cells were incubated with H1975-Spike cells at a 1:1 cell ratio in a U-bottom 96-well plate in the presence of ACE2-Fc, ACE2, or control (Dulbecco's Phosphate-Buffered Saline (DPBS, Corning®). Two microliters of the antihuman CD107a antibody (BioLegend, H4A3) was mixed into each well. The plate was then centrifuged at 200 g for 5 min to facilitate the contact of NK cells and H1975-Spike cells. After 1 h of incubation at 37° C., Brefeldin A and Monensin mixtures (BioLegend) were added into each well, and the plate was incubated at 37° C. for another 3 h. The cells were then fixed and permeabilized with Cyto-Fast Fix-Perm Buffer (BioLegend) and stained with anti-human IFNc (BioLegend, B27) and anti-human TNF-a (BioLegend, MAb11) according to the manufacturer's protocol. The stained cells were resuspended in flow cytometry buffer and analyzed by the Cyto-FLEX flow cytometer (Beckman Coulter).

Figure 9A:
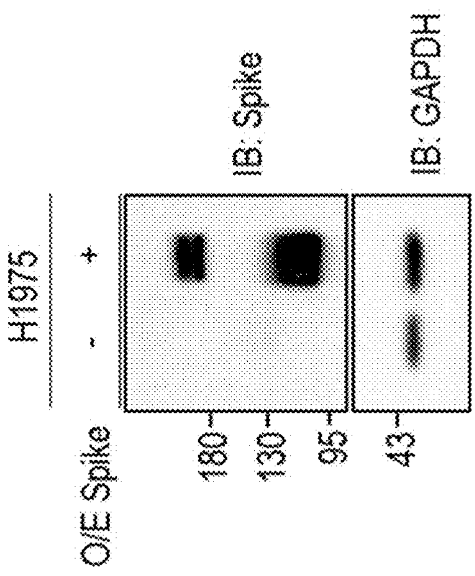
FIGS. 9A-9E include diagrams depicting the effects of ACE2-Fc on NK cell degranulation.
Figure 9B:
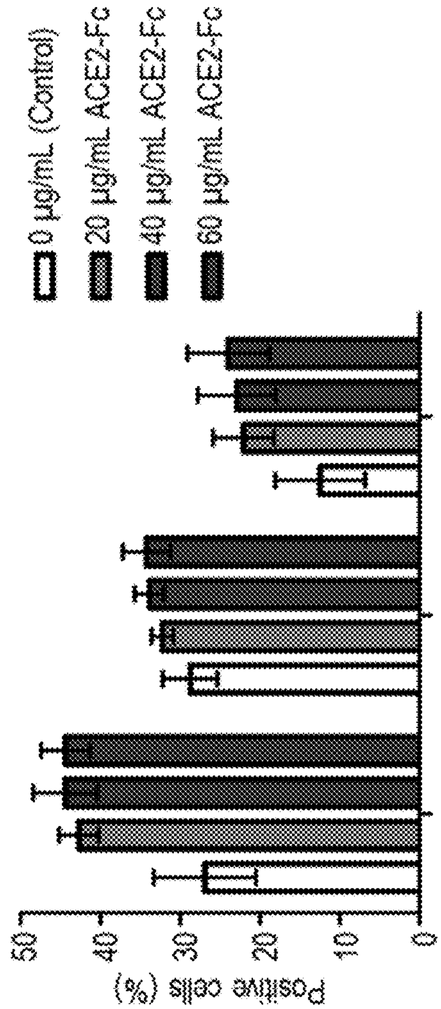
Figure 9E:
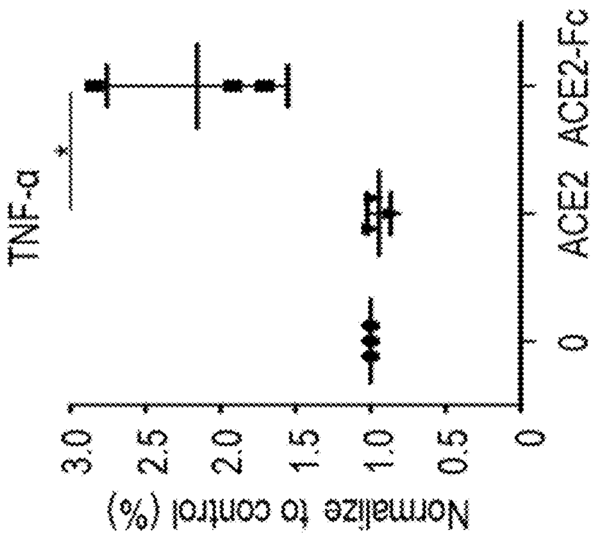
Figure 9D:
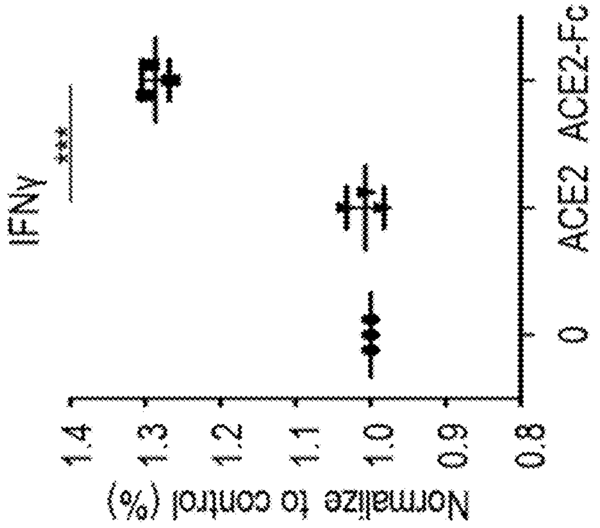
Figure 9C:
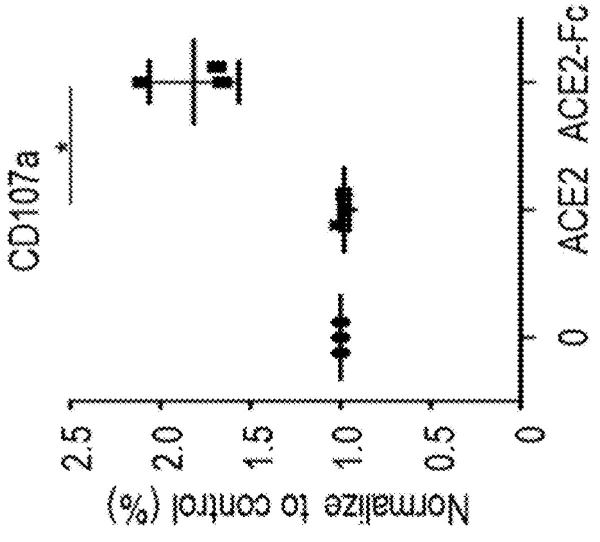

H1975 cells, transduced with full length Spike by the lentiviral vector (H1975-Spike), were used as target cells (FIG. 9A). The NK cell degranulation assay was performed to determine the CD107a, IFN-c, and TNF-α expression levels after the co-incubation of the NK cells with H1975-Spike cells in the presence of ACE2-Fc or recombinant ACE2 (1-740 amino acid residues without an Fc tag). Forty-eight hours before the assay, NK cells were activated by 1,000 U/ml recombinant human IL-2 (Peprotech). To initiate cytotoxicity, 50,000 NK cells were incubated with H1975-Spike cells at a 1:1 cell ratio in a U-bottom 96-well plate in the presence of ACE2-Fc, ACE2, or control (Dulbecco's Phosphate-Buffered Saline (DPBS, Corning®)). Two microliters of the antihuman CD107a antibody (BioLegend, H4A3) was mixed into each well. The plate was then centrifuged at 200 g for 5 min to facilitate the contact of NK cells and H1975-Spike cells. After 1 h of incubation at 37° C., Brefeldin A and Monensin mixtures (BioLegend) were added into each well, and the plate was incubated at 37° C. for another 3 h. The cells were then fixed and permeabilized with Cyto-Fast Fix-Perm Buffer (BioLegend) and stained with anti-human IFNc (BioLegend, B27) and anti-human TNF-a (BioLegend, MAb11) according to the manufacturer's protocol. The stained cells were re-suspended in flow cytometry buffer and analyzed by the Cyto-FLEX flow cytometer (Beckman Coulter). Induction of the expression levels of these three degranulation markers was observed when serially diluted ACE2-Fc was added to the co-culture of NK and H1975-Spike cells (FIGS. 9B-9E). In contrast, the degranulation of NK cells was not observed in the presence of recombinant ACE2. Taken together, these results suggest that ACE2-Fc could not only block SARS-CoV-2 infection but also induce NK cell activation, which may help to remove the infected cells in vivo.

The differential expression of degranulation markers after the treatment of ACE2-Fc or ACE2 is determined by flow cytometry and the results are shown in Table 2 below.

TABLE 2

| | Level of Cells with Positive Expression of Degranulation Markers | | |
|---|---|---|---|
| | CD107+ Cells | IFNγ+ Cells | TNFα+ Cells |
| NK Cells only | 5.81% | 0.28% | 2.15% |
| Control (0 μg/ml) | 21.91% | 18.50% | 9.29% |
| 40 μg/ml ACE2 | 20.91% | 18.36% | 8.49% |
| 40 μg/ml ACE2-Fc | 47.13% | 26.03% | 25.55% |

These findings suggest that the decoy ACE2-Fc fusion protein could block SARS-CoV-2 entry and inhibit viral replication. The ACE2-Ig (1-740 amino acid residues) or non-catalytic mutant form have been reported to block pseudotyped virus infection (Lei et al, 2020*; Nat Commun* 11: 2070). This study's results demonstrated that even when ACE2 was shortened to 597 amino acid residues, the fusion protein still exhibited the peptidase activity as well as the ability to block the entry of real virus, SARS-CoV-2 from clinical isolate, and prevent its infection.

Figure 10:
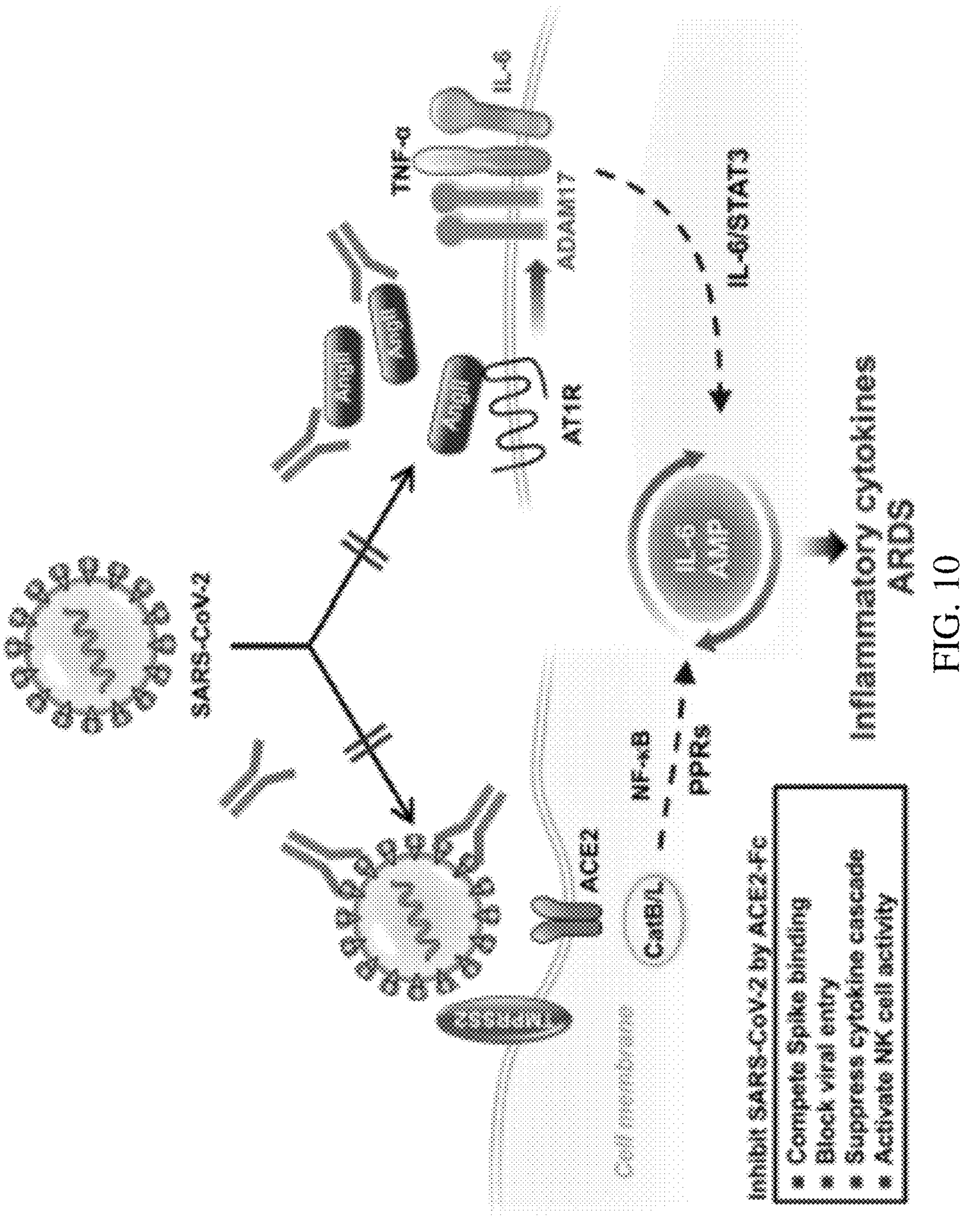
FIG. 10 is a diagram depicting the proposed model for the role of the decoy antibody ACE2-Fc in SARS-CoV-2 entry and infection. The decoy antibody (ACE2-Fc) not only reduces SARS-CoV-2 infection but also decreases TNF-a secretion and ADAM-17 phosphorylation mediated by angiotensin II. Ang II: angiotensin II; ARDS: acute respiratory distress syndrome; CatB/L: cathepsin B and L; PPRs: pattern recognition receptors; AMP: amplifier; STATS: Signal transducer and activator of transcription 3; ATIR: angiotensin II type I receptor; ADAM17: a disintegrin and metalloprotease 17; TMPRSS2: transmembrane Serine Protease 2.

Taken together, data from the Examples disclosed herein provide evidence that the decoy protein, ACE2-Fc, significantly reduced SARS-CoV-2 infection compared with human normal IgG in vitro as illustrated in FIG. 10. The ACE2-Fc fusion protein had a much longer elimination phase half-life compared with recombinant ACE2 (rACE2): 174.2 hours versus 1.8 hours (Liu et al., 2018). The rACE2 and ACE2-Fc had a short and similar distribution phase, ~10-18 minutes. In addition to identify infected host cells and to provide the opportunity for the immune system to clean the injured cells, this ACE2-Fc decoy protein may also provide great potential to develop effective therapeutics against SARS-CoV-2 infection.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art.

Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A fusion polypeptide, comprising:

(i) a fragment of an angiotensin-converting enzyme 2 (ACE2) receptor, wherein the fragment comprises at least one binding site for a spike protein of a coronavirus; and (ii) a Fc region of an immunoglobulin;

wherein the fusion polypeptide binds the coronavirus and suppresses its entry into host cells via the ACE2 receptor, wherein the fusion polypeptide comprises the amino acid sequence of SEQ ID NO:4.

2. The fusion polypeptide of claim 1, wherein the ACE2 receptor is a human ACE2 receptor.

3. The fusion polypeptide of claim 1, wherein the fragment of the ACE2 receptor comprises the ectodomain of the ACE2 receptor.

4. The fusion polypeptide of claim 3, wherein the ACE2 receptor comprises the amino acid sequence of SEQ ID NO:2.

5. The fusion polypeptide of claim 1, which further comprises a signaling peptide at the C-terminus.

6. The fusion polypeptide of claim 1, wherein the immunoglobulin is a human IgG1 molecule or a human IgG4 molecule.

7. The fusion polypeptide of claim 6, wherein the Fc region of the immunoglobulin comprises the amino acid sequence of SEQ ID NO:3.

8. The fusion polypeptide of claim 1, wherein the fragment of the ACE receptor and the Fc fragment are linked via a peptide linker, which is VEVD (SEQ ID NO: 5).

9. The fusion polypeptide of claim 1, wherein the coronavirus is SARS-COV-2.

10. The fusion polypeptide of claim 1, wherein the fusion polypeptide is conjugated with a therapeutic agent, which is an anti-viral agent.

11. An isolated nucleic acid, comprising a nucleotide sequence encoding a fusion polypeptide set forth in claim 1.

12. The isolated nucleic acid of claim 11, which is a vector; optionally wherein the vector is an expression vector.

13. A host cell comprising the nucleic acid of claim 11.

14. The host cell of claim 13, which is a bacterial cell, a yeast cell, an insect cell, or a mammalian cell.

15. A pharmaceutical composition, comprising a fusion polypeptide set forth in claim 1, or a nucleic acid encoding the fusion polypeptide and a pharmaceutically acceptable carrier.

* * * * *